US008133679B2

(12) United States Patent
Muchowski et al.

(10) Patent No.: US 8,133,679 B2
(45) Date of Patent: Mar. 13, 2012

(54) METHODS OF IDENTIFYING AGENTS THAT DIMINISH CELLULAR TOXICITY ASSOCIATED WITH AN α-SYNUCLEIN POLYPEPTIDE OF PARKINSON'S DISEASE IN YEAST

(75) Inventors: Paul J. Muchowski, Kenmore, WA (US); Susan L. Lindquist, Chestnut Hill, MA (US); Tiago Outeiro, Cambridge, MA (US)

(73) Assignees: Whitehead Institute for Biomedical Research, Cambridge, MA (US); University of Washington, Seattle, WA (US)

( * ) Notice: Subject to any disclaimer, the term of this patent is extended or adjusted under 35 U.S.C. 154(b) by 0 days.

(21) Appl. No.: 12/272,031

(22) Filed: Nov. 17, 2008

(65) Prior Publication Data

US 2009/0068111 A1   Mar. 12, 2009

Related U.S. Application Data

(62) Division of application No. 11/003,216, filed on Dec. 3, 2004, now Pat. No. 7,452,670.

(60) Provisional application No. 60/527,215, filed on Dec. 4, 2003.

(51) Int. Cl.
C12Q 1/68        (2006.01)
G01N 33/53      (2006.01)
G01N 33/569    (2006.01)
A01N 63/00      (2006.01)
A01N 63/04      (2006.01)
C07H 21/04      (2006.01)
C12N 15/11      (2006.01)

(52) U.S. Cl. ....... 435/6.13; 435/375; 435/7.31; 435/6.1; 424/93.5; 536/23.1; 536/23.5; 514/44 A

(58) Field of Classification Search .................. None
See application file for complete search history.

(56) References Cited

U.S. PATENT DOCUMENTS

2009/0099069 A1*  4/2009  Lindquist et al. ............... 514/12
2009/0304664 A1* 12/2009  Lindquist et al. ............ 424/94.5

FOREIGN PATENT DOCUMENTS

WO    WO 02/065136    8/2002

OTHER PUBLICATIONS

U.S. Appl. No. 12/781,591, filed May 2010, Lindquist et al.*
U.S. Appl. No. 12/809,859, filed Jun. 2010, Lindquist et al.*
Ambrose et al., "Structure and expression of the Huntington's disease gene: evidence against simple inactivation due to an expanded CAG repeat," Somat. Cell Mol. Genet. 20:27-38 (1994).
Clayton and George, "Synucleins in synaptic plasticity and neurodegenerative disorders," J. Neurosci. Res. 58:120-129 (1999).
Cummings et al., "Over-expression of inducible HSP70 chaperone suppresses neuropathology and improves motor function in SCAI mice," Hum. Mol. Genet. 10:1511-1518 (2001).
Engelender et al., "Synphilin-1 associates with .alpha.-synuclein and promotes the formation of cytosolic inclusions," Nat. Genet. 22:110-114 (1999).
Fernandez-Funez et al., "Identification of genes that modify ataxin-1-induced neurodegeneration," Nature 408:101-106 (2000).
George et al., "Characterization of a novel protein regulated during the critical period for song learning in the zebra finch," Neuron 15:361-372 (1995).
Goedert, "Alpha-synuclein and neurodegenerative diseases," Nat. Rev. Neurosci. 2:492-501 (2001).
Grunenfelder and Winzeler, "Treasures and traps in genome-wide data sets: case examples from yeast," Nat. Rev. Genet. 3:653-61 (2002).
Gusella and MacDonald, "Molecular genetics: unmasking polyglutamine triggers in neurodegenerative disease," Nat. Rev. Neurosci. 1:109-115 (2000).
Hardy and Selkoe, "The amyloid hypothesis of Alzheimer's disease: progress and problems on the road to therapeutics," Science 297:353-356 (2002).
Huntington's Disease Collaborative Research Group, "A novel gene containing a trinucleotide repeat that is expanded and unstable on Huntington's disease chromosomes," Cell 72:971-983 (1993).
Kazemi-Esfarjani and Benzer, "Genetic suppression of polyglutamine toxicity in *Drosophila*," Science 287:1837-1840 (2000).
Kruger et al., "Ala30Pro mutation in the gene encoding .alpha.-synuclein in Parkinson's disease," Nat. Genet. 18:106-08 (1998).
Lotharius and Brandin, "Pathogenesis of Parkinson's disease: dopamine, vesicles and .alpha.-synuclein," Nat. Rev. Neurosci. 3:932-942 (2002).
Moore et al. Annu. Rev. Neurosci. 28:57-87 (2005).
Muchowski et al., "Hsp70 and hsp40 chaperones can inhibit self-assembly of polyglutamine proteins into amyloids-like fibrils," Proc. Natl. Acad. Sci. USA97:7841-7846 (2000).
Polymeropoulos et al., "Mutation in the alpha-synuclein gene identified in families with Parkinson's Disease," Science 276:2045-2047 (1997).
Rochet and Lansbury Jr., "Amyloid Fibrillogenesis: themes and variations," Curr. Opin. Struct. Biol. 10:60-88 (2000).
Scherzinger et al., "Huntington-encoded polyglutamine expansions form amyloid-like protein aggregates in vitro and in vivo," Cell 90:549-558 (1997).
Volles et al., "Vesicle permeabilization by protofibrillar .alpha.-synuclein: implications for the pathogenesis and treatment of Parkinson' disease," Biochemistry 40:7812-7819 (2001).
Warrick et al., "Suppression of polyglutamine-mediated neurodegeneration in *Drosophila* by the molecular chaperone HSP70," Nat. Genet. 23:425-428 (1999).
Zoghbi and Orr, "Glutamine repeats and neurodegeneration," Ann. Rev. Neurosci. 23:217-247 (2000).

* cited by examiner

*Primary Examiner* — Chang-Yu Wang
(74) *Attorney, Agent, or Firm* — Fish & Richardson P.C.

(57) ABSTRACT

Methods of screening candidate agents to identify lead compounds for the development of therapeutic agents for the treatment of a neurodegenerative disease, such as Huntington's Disease and Parkinson's Disease and methods for identifying a mutation in, or changes in expression of, a gene associated with neurodegenerative disease, such as Huntington's Disease and Parkinson's Disease, are provided.

10 Claims, No Drawings

METHODS OF IDENTIFYING AGENTS THAT DIMINISH CELLULAR TOXICITY ASSOCIATED WITH AN α-SYNUCLEIN POLYPEPTIDE OF PARKINSON'S DISEASE IN YEAST

CROSS-REFERENCES TO RELATED APPLICATIONS

The present application is a divisional of U.S. application Ser. No. 11/003,216, filed Dec. 3, 2004, which claims benefit to U.S. Provisional Application No. 60/527,215, filed Dec. 4, 2003. The entire content of the prior applications are incorporated herein by reference.

BACKGROUND OF THE INVENTION

Huntington's disease (HD) is a fatal, inherited neurodegenerative disorder that is characterized by disturbances in movement, cognition and personality. HD is autosomal dominant. Neurodegeneration is associated with selective neuronal cell death, occurring primarily in the cortex and striatum of the brain.

The mutation that causes HD is an expansion of CAG repeats in the first exon of gene IT-15, that encodes the huntingtin protein (Huntington's Disease Collaborative Research Group, *Cell* 72:971-83 (1993); Ambrose et al., *Somat. Cell Mol. Genet.* 20:27-38 (1994)). CAG encodes the amino acid glutamine ("Gln" or "Q"), so CAG repeats encode polyglutamine (or "polyQ") regions within huntingtin. The polyglutamine region of huntingtin from non-HD individuals contains about 8-31 consecutive Gln residues. Huntingtin with over 37 consecutive Gln residues is associated with mild to severe HD, with the more severe cases exhibiting a polyglutamine region of up to about 68, or more, Gln residues. The same mutational mechanism, expansion of CAG repeats, is responsible for a growing number of less common neurodegenerative disorders that include the spinocerebellar ataxias (SCAs) (Zoghbi et al., *Ann. Rev. Neurosci.* 23:217-47 (2000)).

Parkinson's disease (PD) is a major neurodegenerative disorder characterized by muscle rigidity, bradykinesia, resting tremor and postural instability (Goedert, *Nat. Rev. Neurosci.* 2:492-501 (2001)). Although the vast majority of cases of PD are idiopathic, a small percentage of cases are caused by missense mutations in the α-synuclein gene (Polymeropoulos et al., *Science* 276:2045-47 (1997); Kruger et al., *Nat. Genet.* 18:106-08 (1998)). One neuropathological feature shared by both HD and PD is the occurrence of ubiquitinated inter-neuronal inclusion bodies in diseased brains. Huntingtin and/or degradation products of huntingtin are the major components of cytoplasmic and nuclear inclusion bodies that are observed in HD. α-Synuclein is the major component of inclusion bodies (called Lewy bodies) in PD.

Huntingtin and α-synuclein assemble into fibrillar protein aggregates that display many properties of amyloid in vitro and in vivo (Scherzinger et al., *Cell* 90:549-58 (1997); Rochet et al., *Curr. Opin. Struct. Biol.* 10:60-88 (2000)). The "amyloid hypothesis," developed originally to describe the role of β-amyloid in Alzheimer's Disease (AD), suggests that the aggregation of proteins into an ordered fibrillar structure is causally related to aberrant protein interactions that culminate in neuronal dysfunction and cell death (Hardy et al., *Science* 297:353-56 (2002)). The similar physical, biochemical and morphological features of huntingtin, α-synuclein and other amyloid-forming proteins have led to the speculation that neurodegeneration associated with protein misfolding may have common molecular mechanisms. However, the precise roles of protein aggregation, amyloid formation and inclusion bodies in HD, PD, and other amyloid diseases remain controversial. While significant efforts have been made to understand the roles of huntingtin and α-synuclein in HD and PD, respectively, a unifying pathogenic mechanism has not been identified. Different genes and pathways have been suggested to play important roles in PD and HD (see, e.g., Goedert, *Nat. Rev. Neurosci.* 2:492-501 (2001); Gusella et al., *Nat. Rev. Neurosci.* 1:109-15 (2000)), but these suggestions remain to be confirmed. Further, the lack of tractable genetic models has impeded the identification of additional genes involved in, or associated with, neurotoxicity.

BRIEF SUMMARY OF THE INVENTION

The present invention provides methods of identifying a potential therapeutic agent for the treatment of a neurodegenerative disease (e.g., Parkinson's disease or Huntington's disease). The methods generally include the following steps: (1) contacting a eukaryotic cell with a candidate agent, where the cell expresses a neurotoxic polypeptide and does not express an endogenous wild-type gene which causes or enhances toxicity in the presence of the neurotoxic polypeptide, and where expression of the neurotoxic polypeptide is toxic to the cell; and (2) determining whether the candidate agent reduces toxicity of the neurotoxic polypeptide on the cell, whereby if the candidate agent reduces toxicity of the neurotoxic polypeptide on the cell, the candidate agent is identified as a potential therapeutic agent. In some embodiments, the neurotoxic polypeptide is a huntingtin polypeptide comprising an expanded polyQ repeat (e.g., a polyQ repeat having at least 45 glutamine residues), α-synuclein, a fusion protein (e.g., a fusion protein comprising a myc epitope), or a reporter polypeptide. Further, the eukaryotic cell can be a yeast cell (e.g., a *Saccharomyces cerevisiae* cell), rat cell, mouse cell, *Drosophila* cell, or *C. elegans* cell. In certain embodiments where the method is an in vitro method, the cell is a human cell. The cell can have, for example, a null allele of the wild-type gene, or a deletion of the wild-type gene.

In a specific embodiment, the neurotoxic polypeptide is a huntingtin polypeptide comprising an expanded polyQ repeat and the cell is a *Saccharomyces cerevisiae* cell that does not express at least one endogenous wild-type gene selected from apj1, apm2, aro9, ayr1, cit2, cmk1, cos111, cps1, dcg1, fil1, fpr2, gda1, glo2, gre2, gsh2, hlj1, hlr1, hms1, ipk1, kgd1, msb1, mrpl1, mup1, npt1, pcl6, phm8, prm5, psp1, rim4, sam2, sas3, sdt1, sip18, sng1, stp2, tea1, tvp15, ubp13, vps70, yhb1, yrb30, ybr100w, ybr258w, ydr215c, ygr015c, jlr107w, ykr017c, ykr064, ylr128w, ymr160w, ynl296w, yor292c, yor300w and ypl067c. For example, in certain embodiments, the cell does not express at least two endogenous wild-type genes selected from apj1, apm2, aro9, ayr1, cit2, cmk1, cos111, cps1, dcg1, fil1, fpr2, gda1, glo2, gre2, gsh2, hlj1, hlr1, hms1, ipk1, kgd1, msb1, mrpl1, mup1, npt1, pcl6, phm8, prm5, psp1, rim4, sam2, sas3, sdt1, sip18, sng1, stp2, tea1, tvp15, ubp13, vps70, yhb1, yrb30, ybr100w, ybr258w, ydr215c, ygr015c, jlr107w, ykr017c, ykr064, ylr128w, ymr160w, ynl296w, yor292c, yor300w and ypl067c.

In another specific embodiment, the neurotoxic polypeptide is an α-synuclein polypeptide and the cell is a *Saccharomyces cerevisiae* cell that does not express at least one endogenous wild-type gene selected from ape2, arl3, arol, cog6, crh1, cvt17, dpp1, fun26, gip2, glo4, gtt1, hbs1, hsp30, ino4, mad1, mal31, mei4, met17, met32, msb3, nbp2, nit2, nup53, opi3, pca1, pex2, pex8, pho13, pox1, ptk2, rpl41a, rny1, sac2, sap4, sod2, stf1, stp2, suv3, swr1, thi7, tlg2, thrl, tna1, tsl1, ubc8, vps24, vps28, vps60, war1, yat1, ybr013c, ybr284w, ybr300c, ycl1042w, ycr026c, ycr050c, ycr051w, ycr085w, ydl118w, ydr154c, ydr220c, ygl109w, ygl165c, ygl226w, ygl231c, ygl262w, ygr130c, ygr154c, ygr201c, ygr290w, yhr199c, yjl118w, yjl122w, yjl135w, yjrl54w, ykl098w, ykl100c, ykr023w, ykr035c, yrl365w, ylr376c, ymr226c, yml089c, ymr289w and yp136w. For example, in certain embodiments, the cell does not express at least two endogenous wild-type genes selected from ape2, arl3, arol, cog6, crhl, cvt17, dpp1, fun26, gip2, glo4, gtt1, hbs1, hsp30, ino4, mad1, mal31, mei4, met17, met32, msb3, nbp2, nit2, nup53, opi3, pca1, pex2, pex8, pho13, pox1, ptk2, rpl41a, rny1, sac2, sap4, sod2, stf1, stp2, suv3, swr1, thi7, tlg2, thrl, tna1, tsl1, ubc8, vps24, vps28, vps60, war1, yat1, ybr013c, ybr284w, ybr300c, yc1042w, ycr026c, ycr050c, ycr051w, ycr085w, ydl118w, ydr154c, ydr220c, ygl109w, ygl165c, ygl226w, ygl231c, ygl262w, ygr130c, ygr154c, ygr201c, ygr290w, yhr199c, yjl118w, yjl122w, yjl135w, yjrl54w, ykl098w, ykl100c, ykr023w, ykr035c, yrl365w, ylr376c, ymr226c, yml089c, ymr289w and yp136w.

The candidate agent can be a synthetic compound or a natural compound. In certain embodiments, the candidate agent is a small molecule, a nucleic acid, a proteinaceous agent, or a peptidomimetic. Further, the contacting of the cell with the candidate agent can include transformation or culturing the cell in media containing the candidate agent.

In some embodiments, the method of identifying a potential therapeutic agent includes comparing the viability of the cell contacted with the candidate agent with the viability of a control cell contacted with the candidate agent, where the control cell expresses the neurotoxic polypeptide and the wild-type gene. In yet other embodiments, the method includes comparing the viability of the cell contacted with the candidate agent with the viability of a control cell not contacted with the candidate agent, where the control cell does not express the neurotoxic polypeptide or the wild-type gene.

In specific embodiments, the method is a method for identifying a potential therapeutic agent for Parkinsons disease, the neurotoxic polypeptide is an α synuclein polypeptide, and the cell is a yeast cell. The α-synuclein polypeptide can be, e.g., a wild-type α-synuclein polypeptide or a mutant α-synuclein polypeptide. The method can further include re-screening at least one identified candidate agent to confirm that the identified agent reduces toxicity of the α-synuclein polypeptide. For example, in some embodiments, the re-screening includes contacting a second yeast cell with the candidate agent, wherein the second yeast cell expresses the α synuclein polypeptide and does not express the endogenous wild-type gene which causes or enhances toxicity in the presence of the α synuclein polypeptide, and where expression of the α synuclein polypeptide is toxic to the second yeast cell; and determining whether the candidate agent reduces toxicity of the α synuclein polypeptide on the second yeast cell. Further, in certain embodiments, the method also includes administering the potential therapeutic agent to an animal model of Parkinson's disease, and determining whether the potential therapeutic agent prevents or reduces a symptom of Parkinson's disease in the animal model. In yet other embodiments, where the yeast cell is a *Saccharomyces cerevisiae* cell, the yeast cell does not express at least one endogenous wild-type gene selected from ape2, arl3, arol, cog6, crhl, cvt17, dpp1, fun26, gip2, glo4, gtt1, hbs1, hsp30, ino4, mad1, mal31, mei4, met17, met32, msb3, nbp2, nit2, nup53, opi3, peal, pex2, pex8, pho13, pox1, ptk2, rpl41a, rny1, sac2, sap4, sod2, stf1, stp2, suv3, swr1, thi7, tlg2, thrl, tna1, tsl1, ubc8, vps24, vps28, vps60, war1, yat1, ybr013c, ybr284w, ybr300c, yc1042w, ycr026c, ycr050c, ycr051w, ycr085w, ydl118w, ydr154c, ydr220c, ygl109w, ygl165c, ygl226w, ygl231c, ygl262w, ygr130c, ygr154c, ygr200c, ygr290w, yhr199c, yjl118w, yjl122w, yjl135w, yjrl54w, ykl098w, ykl100c, ykr023w, ykr035c, yrl365w, ylr376c, ymr226c, yml089c, ymr289w and yp136w. In some embodiments, the yeast cell does not express at least two endogenous wild-type genes selected from ape2, arl3, arol, cog6, crhl, cvt17, dpp1, fun26, gip2, glo4, gtt1, hbs1, hsp30, ino4, mad1, mal31, mei4, met17, met32, msb3, nbp2, nit2, nup53, opi3, peal, pex2, pex8, pho13, pox1, ptk2, rpl41a, rny1, sac2, sap4, sod2, stf1, stp2, suv3, swr1, thi7, tlg2, thrl, tna1, tsl1, ubc8, vps24, vps28, vps60, war1, yat1, ybr013c, ybr284w, ybr300c, ycl042w, ycr026c, ycr050c, ycr051w, ycr085w, ydl118w, ydr154c, ydr220c, ygl109w, ygl165c, ygl226w, ygl231c, ygl262w, ygr130c, ygr154c, ygr201c, ygr290w, yhr199c, yjl118w, yjl122w, yjl135w, yjrl54w, yk098w, ykl100c, ykr023w, ykr035c, yrl365w, ylr376c, ymr226c, yml089c, ymr289w and yp136w.

In other specific embodiments, the method is a method for identifying a potential therapeutic agent for Huntington's disease, the neurotoxic polypeptide is a huntingtin polypeptide, and the cell is a yeast cell. The huntingtin polypeptide can be, e.g., a wild-type huntingtin polypeptide or a mutant huntingtin polypeptide. In certain embodiments, the huntingtin polypeptide comprises an expanded polyQ repeat. The method can further include re-screening at least one identified candidate agent to confirm that the identified agent reduces toxicity of the huntingtin polypeptide. For example, in some embodiments, the re-screening includes contacting a second yeast cell with the candidate agent, wherein the second yeast cell expresses the huntingtin polypeptide and does not express the endogenous wild-type gene which causes or enhances toxicity in the presence of the huntingtin polypeptide, and where expression of the huntingtin polypeptide is toxic to the second yeast cell; and determining whether the candidate agent reduces toxicity of the huntingtin polypeptide on the second yeast cell. Further, in certain embodiments, the method also includes administering the potential therapeutic agent to an animal model of Huntington's disease, and determining whether the potential therapeutic agent prevents or reduces a symptom of Huntington's disease in the animal model. In yet other embodiments, where the yeast cell is a *Saccharomyces cerevisiae* cell, the yeast cell does not express at least one endogenous wild-type gene selected from apj1, apm2, aro9, ayr1, cit2, cmk1, cos111, cps1, dcg1, fil1, fpr2, gda1, glo2, gre2, gsh2, hlj1, hlr1, hms1, ipk1, kgd1, msb1, mrpl1, mup1, npt1, pcl6, phm8, prm5, psp1, rim4, sam2, sas3, sdt1, sip18, sng1, stp2, tea1, tvp15, ubp13, vps70, yhb1, yrb30, ybr100w, ybr258w, ydr215c, ygr015c, jlr107w, ykr017c, ykr064, ylr128w, ymr160w, ynl296w, yor292c, yor300w and ypl067c. In some embodiments, the yeast cell does not express at least two endogenous wild-type genes selected from apj1, apm2, aro9, ayr1, cit2, cmk1, cos111, cps1, dcg1, fil1, fpr2, gda1, glo2, gre2, gsh2, hlj1, hlr1, hms1, ipk1, kgd1, msb1, mrpl1, mup1, npt1, pcl6, phm8, prm5, psp1, rim4, sam2, sas3, sdt1, sip18, sng1, stp2, tea1, tvp15, ubp13, vps70, yhb1, yrb30, ybr100w, ybr258w, ydr215c, ygr015c, jlr107w, ykr017c, ykr064, ylr128w, ymr160w, ynl296w, yor292c, yor300w and ypl067c.

In another aspect, the present invention provides methods of identifying a gene that reduces the toxicity of a neurotoxic polypeptide in a yeast cell. The methods of identifying a gene generally include the following steps: (1) providing a yeast cell which expresses the neurotoxic polypeptide and does not express a first endogenous wild-type gene which causes or enhances toxicity in the presence of the neurotoxic polypeptide, where expression of the neurotoxic polypeptide is toxic to the cell; (2) inactivating a second wild-type in the yeast cell; and (3) determining whether the inactivation of the second wild-type gene reduces toxicity of the neurotoxic polypeptide in the yeast cell. In certain embodiments, the inactivation of the second wild-type gene is by gene disruption. In other embodiments, the inactivation of the second wild-type is by replacement of the second wild-type gene with a null allele of the second wild-type gene. For example, in some embodiments, the second wild-type gene is replaced by mating the yeast strain expressing the neurotoxic polypeptide with a yeast strain of suitable mating type and comprising the null allele of the second wild-type gene, thereby producing a diploid yeast strain; the resulting diploid yeast strain is then sporulated and progeny are analyzed to determine whether inactivation of the second wild-type gene reduces toxicity of the neurotoxic polypeptide in the yeast cell.

In another aspect, the present invention provides yeast strains having a nucleic acid encoding a huntingtin polypeptide and not expressing an endogenous wild-type gene which causes or enhances toxicity in the presence of the huntingtin polypeptide, where the huntingtin polypeptide is toxic to the yeast cell when expressed; and where the wild-type yeast gene is at least one of apj1, apm2, aro9, ayr1, cit2, cmk1, cos111, cps1, dcg1, fil1, fpr2, gda1, glo2, gre2, gsh2, hlj1, hlr1, hms1, ipk1, kgd1, msb1, mrpl1, mup1, npt1, pcl6, phm8, prm5, psp1, rim4, sam2, sas3, sdt1, sip18, sng1, stp2, tea1, tvp15, ubp13, vps70, yhb1, yrb30, ybr100w, ybr258w, ydr215c, ygr015c, jlr107w, ykr017c, ykr064, ylr128w, ymr160w, ynl296w, yor292c, yor300w and ypl067c.

In another aspect, the present invention provides yeast strains comprising a nucleic acid encoding an α-synuclein polypeptide and not expressing an endogenous wild-type gene which causes or enhances toxicity in the presence of the α synuclein polypeptide, where the α-synuclein polypeptide is toxic to the yeast cell when expressed; and where the wild-type yeast gene is at least one of ape2, arl3, arol, cog6, crhl, cvt17, dpp1, fun26, gip2, glo4, gtt1, hbs1, hsp30, ino4, mad1, mal31, mei4, met17, met32, msb3, nbp2, nit2, nup53, opi3, pca1, pex2, pex8, pho13, pox1, ptk2, rpl41a, rny1, sac2, sap4, sod2, stp1, stp2, suv3, swr1, thi7, tlg2, thrl, tna1, tsl1, ubc8, vps24, vps28, vps60, war1, yat1, ybr013c, ybr284w, ybr300c, ycl042w, ycr026c, ycr050c, ycr051w, ycr085w, ydl118w, ydr154c, ydr220c, ygl109w, ygl165c, ygl226w, ygl231c, ygl262w, ygr130c, ygr154c, ygr201c, ygr290w, yhr199c, yjl118w, yjl122w, yjl135w, yjr154w, ykl098w, ykl100c, ykr023w, ykr035c, yrl365w, ylr376c, ymr226c, yml089c, ymr289w and yp136w.

In yet another aspect, the present invention provides methods of identifying a polymorphism, in a human gene, correlated with a predisposition in a human to developing a neurodegenerative disease. In certain embodiments, the neurodegenerative disease is Huntington's disease or Parkinson's disease. The methods for identifying the polymorphism generally include the following steps: (1) obtaining a plurality of biological samples from a plurality of human subjects having or at risk for developing the neurodegenerative disease, the biological samples comprising nucleic acids; (2) analyzing nucleic acids obtained from the biological samples to determine whether a polymorphism is present in the human gene of the subjects, where the human gene is an ortholog of a yeast gene, the absence of which causes or enhances toxicity of a neurotoxic polypeptide in yeast; and determining whether the mutation in the human gene in a plurality of subjects is correlated with the predisposition in a human to develop the neurodegenerative disease. In certain embodiments, the polymorphism is a single nucleotide substitution. The polymorphism can be, for example, in a promoter region, 5' untranslated region, coding region, intron, 3' untranslated region, or 3' untranscribed regions of the human gene. Further, the polymorphism can be detected by, for example, sequencing genomic DNA segments containing at least a portion of the human gene, by sequencing a cDNA encoding at least a portion of the human gene, or by restriction fragment length polymorphism analysis, allele-specific PCR, ligase chain reaction or single stranded length polymorphism. In specific embodiments, the neurotoxic polypeptide is a huntingtin polypeptide and the human gene is DNAJA2, DNAJA1, DNAJB1, AP1M1, AP1M2, AP2M1, HSD17B1, HSD17B2, RDH8, CS, CKLIK, CAMK1, CAMK1G, FLJ32569, ACY1, FKBP2, FKBP14, FKBP10, ENTPD6, ENTPD5, ENTPD3, HAGH, BRP17, MGC2605, HSD3B1, H105E3, GSS, MGC26226, DNAJA3, TFEB, SREBF1, MITF, OGDH, FLJ10851, KIAA1630, NCOA1, MGC20460, SLC7A9, SLC7A7, SLC7A6, HSU53209, SFRS10, TIAL1, MAT1A, MAT2A, HTATIP, HBOA, RUNXBP2, LOC284459, LOC126295, OAZ, FLJ12552, USP12, USP10, FOLH1, NAALAD2, NGB, HBG1, WBSCR21, ARIH1, ARIH2, RP42, MGC2714, KIAA0276, MPV17, or PXMP2. In other specific embodiments, the neurotoxic polypeptide is an α-synuclein polypeptide and the human gene is NPEPPS, ENPEP, LRAP, ARFRP1, FLJ22595, ARL5, COG6, MUC16, KIAA2026, MUC12, HTPAP, PPAP2A, PPAP2B, ENT3, SLC29A1, SLC29A2, PPP1R3c, PPP1R3B, PPP1R3A, HAGH, MR-1, MGC2605, HBS1L, GSPT2, GSPT1, SLC2A2, SLC2A14, SLC2A3, CTH, FLJ23436, ZNF214, ZNF132, TBC1D8, KIAA1055, EP164, SH3RF, SSH3BP1, SH3GL1, NIT1, NIT2, UPB1, LOC129401, PEMT, ATP7B, ATP7A, ATP12A, PXMP3, DJ37E16.5, ACOX1, ACOX2, ACOX3, SSTK, MARK2, STK22B, RNASE6PL, VPS52, SOD2, LOC284459, MGC43537, SUPV3L1, KIAA0052, DDX27, SRCAP, KIAA1259, EP400, STX16, STX1B2, STX1A, SLC17A5, C20ORF59, UBE2H, UBE2D3, UBE2A, NEDF, BC-2, DKFZP564O123, CPT2, CRAT, CHAT, AMPD2, AMPD1, AMPD3, ENPP5, ENPP3, ENPP1, TNKS2, TNKS, MIB, LOC51234, TGOLN2, RNF111, NEDL2, EEF1G, VARS2, HM13, SPPL2B, SPPL2A, TRIP4, RDH8, MGC417 or RETSDR2.

In still another aspect, the present invention provides methods for detecting a change in expression of a human gene associated with a predisposition to a neurodegenerative disease. The methods generally include (1) obtaining biological samples from a plurality of subjects having or at risk for developing a neurodegenerative disease, the biological samples comprising nucleic acids, where the neurodegenerative disease is Huntington's disease or Parkinson's disease; and (2) analyzing the samples to determine an expression level of the human gene in the subjects, where the human gene is an ortholog of a yeast gene, the absence of which causes or enhances toxicity of a neurotoxic polypeptide in yeast; and (3) comparing the expression levels of the human gene in the subjects with the expression level of the human gene in a human subject not having or at risk for developing the neurodegenerative disease to determine whether a difference in expression of the human gene is correlated with a predisposition in a human having the neurodegenerative disease. In specific embodiments, the neurotoxic polypeptide is a huntingtin polypeptide and the human gene is DNAJA2, DNAJA1, DNAJB1, APIM1, AP1M2, AP2M1, HSD17B1, HSD17B2, RDH8, CS, CKLIK, CAMK1, CAMK1G, FLJ32569, ACY1, FKBP2, FKBP14, FKBP10, ENTPD6, ENTPD5, ENTPD3, HAGH, BRP17, MGC2605, HSD3B1, H105E3, GSS, MGC26226, DNAJA3, TFEB, SREBF1, MITF, OGDH, FLJ10851, KIAA1630, NCOA1, MGC20460, SLC7A9, SLC7A7, SLC7A6, HSU53209, SFRS10, TIAL1, MAT1A, MAT2A, HTATIP, HBOA, RUNXBP2, LOC284459, LOC126295, OAZ, FLJ12552, USP12, USP10, FOLH1, NAALAD2, NGB, HBG1, WBSCR21, ARIH1, ARIH2, RP42, MGC2714, KIAA0276, MPV17, or PXMP2. In other embodiments, the neurotoxic polypeptide is an α-synuclein polypeptide and the human gene is NPEPPS, ENPEP, LRAP, ARFRP1, FLJ22595, ARL5, COG6, MUC16, KIAA2026, MUC12, HTPAP, PPAP2A, PPAP2B, ENT3, SLC29A1, SLC29A2, PPP1R3c, PPP1R3B, PPP1R3A, HAGH, MR-1, MGC2605, HBS1L, GSPT2, GSPT1, SLC2A2, SLC2A14, SLC2A3, CTH, FLJ23436, ZNF214, ZNF132, TBC1D8, KIAA1055, EP164, SH3RF, SSH3BP1, SH3GL1, NIT1, NIT2, UPB1, LOC129401, PEMT, ATP7B, ATP7A, ATP12A, PXMP3, DJ37E16.5, ACOX1, ACOX2, ACOX3, SSTK, MARK2, STK22B, RNASE6PL, VPS52, SOD2, LOC284459, MGC43537, SUPV3L1, KIAA0052, DDX27, SRCAP, KIAA1259, EP400, STX16, STX1B2, STX1A, SLC17A5, C20ORF59, UBE2H, UBE2D3, UBE2A, NEDF, BC-2, DKFZP564O123, CPT2, CRAT, CHAT, AMPD2, AMPD1, AMPD3, ENPP5, ENPP3, ENPP1, TNKS2, TNKS, MIB, LOC51234, TGOLN2, RNF 111, NEDL2, EEF1G, VARS2, HM13, SPPL2B, SPPL2A, TRIP4, RDH8, MGC417 or RETSDR2.

DETAILED DESCRIPTION OF THE INVENTION

The present invention generally relates to eukaryotic cell expression systems and methods for identifying agents that reduce toxicity of an amyloidogenic polypeptide, particularly an amyloidogenic neurotoxic polypeptide (hereinafter "neurotoxic polypeptide"). As used herein, the term "amyloidogenic polypeptide" refers to a protein, polypeptide or peptide that is capable of forming or inducing the formation of protein aggregates or deposits, typically insoluble protein fibrils, either intracellular or extracellularly, or that contains a motif or domain involved in a molecular cascade involved in the formation of such protein aggregates or deposits. Amyloidogenic polypeptides are involved in the etiology and pathology of various amyloidogenic diseases, including, e.g., neurodegenerative diseases (see, e.g., Ross and Poirier, *Nature Medicine* 10 (Supplement):S10-S17, 2004) as well as systemic diseases.

Cell expression systems are provided in which an amyloidogenic polypeptide is expressed in a eukayotic cell in which the polypeptide is toxic. Methods of using the cell expression systems are provided to identify candidate agents that reduce toxicity of the amyloidogenic polypeptide. The identified candidate agents can be used as lead compounds to prepare therapeutic agents for the treatment of amyloidosis (amyloidogenic disease), particularly neurodegenerative disease, such as Huntington's Disease and Parkinson's Disease. The present invention also provides methods of identifying a polymorphism in, or changes in expression of, a gene associated with such amyloidogenic diseases.

In one aspect, eukaryotic cell expression systems and methods are provided for screening candidate agents to identify those agents that reduce toxicity of a neurotoxic polypeptide. The methods utilize a eukaryotic cell expression system to express a neurotoxic polypeptide in which the polypeptide is toxic. The neurotoxic polypeptide is associated with a neurodegenerative disease in humans, such as Huntington's Disease or Parkinson's Disease.

Typically, at least one candidate agent is contacted with at least one cell of the eukaryotic cell expression system expressing the neurotoxic polypeptide to identify at least one candidate agent that modulates toxicity of the neurotoxic polypeptide in the cell. Suitable candidate agents can be, for example, nucleic acids, proteins, polypeptides, peptides, natural agents, synthetic agents, or the like.

The term "neurotoxic polypeptide" refers to an amyloidogenic polypeptide that is neurotoxic when expressed in humans. Neurotoxic effects can be caused by a variety of cellular processes, including protein misfolding, aggregation, mis-localization, accumulation and/or deposition (such as inclusion or Lewy body formation). In humans, a neurotoxic effect can lead to neurodegeneration, which results in a loss of motor control, memory loss, dementia and ultimately death. Typical neurotoxic polypeptides include, for example, huntingtin polypeptide, α-synuclein, and fragments thereof. Other suitable neurotoxic polypeptides are associated with neurotoxic effects in neurodegenerative diseases such as spinocerebellar ataxias, Alzheimer's disease, or the like.

The neurotoxic polypeptide can be full length, substantially full-length, or a functionally equivalent form of the neurotoxic polypeptide. Alternatively, the neurotoxic polypeptide can be a truncated polypeptide or a polypeptide with one or more internal deletions. The neurotoxic polypeptide is typically derived from a human source. In specific embodiments, the neurotoxic polypeptide is a human huntingtin polypeptide, the polypeptide encoded by exon one of human huntingtin gene, or human α-synuclein. In additional embodiments, the neurotoxic polypeptide can be a non-human, mammalian homolog or ortholog of a human neurotoxic polypeptide, or a fragment thereof. In other embodiments, the neurotoxic polypeptide can have an expanded polyQ region. In the example of a huntingtin polypeptide encoded by exon 1, the polypeptide is typically about 68 amino acids in length, excluding polyQ repeats. The polyQ repeats typically are typically about 25 glutamine residues in length in a wild-type huntingtin polypeptide and can be expanded in a mutant huntingtin gene. Mutant huntingtin genes can encode a mutant huntingtin polypeptide having at least 37, at least 45, to at least 70, to at least 100 glutamine residues in a polyQ region. In a huntingtin polypeptide with an expanded polyQ region, the number of polyQ repeats is typically at least about 45 glutamine residues in length. In one specific embodiment, the huntingtin polypeptide having an expanded polyQ repeat includes the first 17 amino acids of exon 1 followed by 103 glutamine residues. (See, e.g., Meriin et al., *J. Cell Biol.* 157:997-1004 (2002).)

The sequence of a neurotoxic polypeptide can also be modified by amino acid substitutions, replacements, insertions, deletions, truncations and other modifications. Typically such modifications can be used to prepare mimics of biologically-occurring polypeptides or to generate suitable targets for screening.

For example, certain amino acids can be substituted for other amino acids in a polypeptide without appreciable loss of neurotoxicity (e.g., ability to aggregate). Such changes can be conservative changes. The following eight groups each contain amino acids that are regarded conservative substitutions for one another: 1) Alanine (A) and Glycine (G); 2) Aspartic acid (D) and Glutamic acid (E); 3) Asparagine (N) and Glutamine (Q); 4) Arginine (R) and Lysine (K); 5) Isoleucine (I), Leucine (L), Methionine (M) and Valine (V); 6) Phenylalanine (F), Tyrosine (Y) and Tryptophan (W); 7) Serine (S) and Threonine (T); and 8) Cysteine (C) and Methionine (M) (see, e.g., Creighton, Proteins, W. H. Freeman and Co., New York (1984)).

In designing modified polypeptides, the hydropathic index of amino acids can be considered (see, e.g., Kyte and Doolittle, *J. Mol. Biol.* 157:105-32 (1982)). Amino acid substitutions can also be made on the basis of hydrophilicity.

A neurotoxic polypeptide also can be a fusion protein comprising a neurotoxic polypeptide or a fragment thereof joined at its N- or C-terminus to a second polypeptide. The second polypeptide can be, for example, an epitope, a selectable protein, an enzyme and the like. For example, the second polypeptide can be beta-galactosidase, green fluorescent protein (GFP), FLAG, Myc, or the like.

A variety of eukaryotic cell expression systems can be used in the methods according to the present invention. A suitable eukaryotic cell expression system is one in which expression of the neurotoxic polypeptide in a suitable genetic background causes toxicity. One model eukaryotic organism, yeast, provides a well-established system for genetic and chemical screening. Many genes can be studied in yeast because they are non-essential under certain growth conditions. In addition, homologs and orthologs of yeast genes can be studied in yeast because such homologs and orthologs often have overlapping functions with the yeast genes, allowing deletion or inactivation of the yeast gene.

Suitable yeast strains which can be used in the context of the present invention include, for example, *Saccharomyces cerevisiae, Saccharomyces uvae, Saccharomyces kluyveri, Schizosaccharomyces pombe, Saccharomyces uvarum, Kluyveromyces lactis, Hansenula polymorpha, Pichia pastoris, Pichia methanolica, Pichia kluyveri, Yarrowia lipolytica, Candida* species such as *Candida utilis* or *Candida cacaoi, Geotrichum* species such as *Geotrichum fermentans*, and the like. In a typical embodiment, the yeast strain is *Saccharomyces cerevisiae.*

Other suitable eukaryotic cell expression systems can include, for example, rat, mouse, *Drosophila*, or *C. elegans*. The eukaryotic cell expression system can be another non-human, animal, insect or lower model system. A suitable eukaryotic cell expression system also can be human cells or cells isolated from such a non-human eukaryotic organism, such as, for example, rat, mouse, *Drosophila*, or *C. elegans* cells cultured in vitro. The eukaryotic cell expression system can be genetically engineered to express a neurotoxic polypeptide. For example, *Drosophila* can be genetically engineered to express a neurotoxic polypeptide that causes toxicity in a suitable genetic background. Alternatively, the system can express an endogenous neurotoxic polypeptide that causes toxicity in a suitable genetic background.

The eukaryotic cell of the eukaryotic cell expression system (e.g., a yeast strain) can optionally include alleles of, or mutations in, genes that facilitate uptake or increase permeability of a candidate agent(s). The eukaryotic cell of the cell expression systems (e.g., a yeast strain) also can optionally include alleles of, or mutations in, genes that reduce or prevent metabolism of a candidate agent(s). For example, a yeast strain can include mutations in one or more of the yeast genes erg6, pdr1 and/or pdr3, which affect membrane efflux pumps and may increase permeability of candidate agents.

The genetic background of the eukaryotic cell expression system is one in which expression of the neurotoxic polypeptide causes toxicity. As used herein, "suitable genetic background" refers to cell having a genetic composition in which the neurotoxic polypeptide is toxic. In certain embodiments, the eukaryotic cell lacks at least one wild-type gene. The absence of the wild-type gene causes or enhances toxicity of the neurotoxic polypeptide when it is expressed in cells of the expression system. The toxic phenotype is typically manifested by a reduced growth rate, growth inhibition and/or cell death. In certain expression systems, expression of the neurotoxic polypeptide causes neurotoxicity.

Typically, the lack of the wild-type gene is due to a null mutation, such as a deletion of all or part of the gene. The absence of the wild-type gene also can be due to a mutation causing a partial loss of function of, a change of function of, or acquisition of a new function, by the gene and its gene product. In additional embodiments, the endogenous wild-type gene causing toxicity or increased toxicity can be inactivated (e.g., a null allele), and the cells can express a homolog or ortholog of the endogenous wild-type gene. The homolog or ortholog can be, for example, a human ortholog of the endogenous gene associated with toxicity, as described herein. The homolog or ortholog also can be a mutant, such as a mutant human gene which causes or enhances toxicity in the cell expression system, or neurotoxicity in humans.

As used herein, "wild-type" refers to the naturally occurring sequence of a nucleic acid at a genetic locus in the genome of an organism, and sequences transcribed or translated from such a nucleic acid. A wild-type gene encodes a gene product which performs the normal function of the gene product. The term "wild-type" polypeptide refers to a protein, polypeptide or peptide encoded by a wild-type gene. A genetic locus can have more than one sequence or allele in a population of individuals, and the term "wild-type" encompasses all such naturally-occurring alleles that encode a gene product performing the normal function.

As used herein the term "polymorphic" means that multiple variants exists (i.e., two or more alleles exist) at a genetic locus in the individuals of a population. The term "polymorphism" refers to a difference between two alleles. The term "mutant" refers to a gene having a change in the sequence of a gene or its encoded gene product (e.g., a protein, polypeptide, or peptide), as a result of which the gene product does not perform a function associated with the wild-type gene product. For example, a huntingtin polypeptide having an expanded polyQ region is a mutant. Similarly, a null allele can be mutant gene. A mutant gene can also contain one or more missense, nonsense and/or frameshift mutations.

As used herein, a "homolog" of a first gene refers to a second, different gene that is substantially identical to the first gene, or that encodes a gene product that is substantially identical to the gene product encoded by the first gene. An "ortholog" of a first gene refers to a second gene from a different organism that is substantially identical to the first gene, or that encodes a gene product that is substantially identical or substantially identical to the gene product encoded by the first gene.

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or "percent identity," in the context of two or more nucleic acids or polypeptide sequences, refer to two or more sequences or subsequences that are the same or have a specified percentage of nucleotides or amino acid residues that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Sequences are "substantially identical" to each other if they are at least 20%, at least 25%, at least 30% or at least 35% identical. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity," in the context of two or more polypeptide sequences, refer to two or more sequences or subsequences that have a specified percentage of amino acid residues that are either the same or similar as defined by a conservative amino acid substitutions (i.e., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, or at least 50% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, for example, by the local homology algorithm of Smith and Waterman (*Adv. Appl. Math.* 2:482 (1970)), by the homology alignment algorithm of Needleman and Wunsch (*J. Mol. Biol.* 48:443 (1970)), by the search for similarity method of Pearson and Lipman (*Proc. Natl. Acad. Sci. USA* 85:2444 ((1988)), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (*J. Mol. Evol.* 35:351-360 (1987)). The method used is similar to the method described by Higgins and Sharp (CABIOS 5:151-153 (1989)). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package (e.g., version 7.0 (Devereaux et al., *Nuc. Acids Res.* 12:387-95 (1984)).

Another example of an algorithm that is suitable for determining percent sequence identity and sequence similarity are the BLAST and BLAST 2.0 algorithms, which are described in Altschul et al. (Nuc. Acids Res. 25:3389-402 (1977)), and Altschul et al. (J. Mol. Biol. 215:403-10 (1990)), respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

Gene homologs and orthologs can also be identified using the HomoloGene resource of NCBI. A homolog or ortholog of a first gene can encode a gene product that has the same or a similar function as the gene product encoded by the first gene. Another indication that two nucleic acid sequences or polypeptides are orthologs is that the heterologous gene can complement (e.g., rescue) a null allele of the endogenous gene in a eukaryotic cell expression system.

As discussed above, a eukaryotic cell of the eukaryotic cell expression system can lack at least one wild-type gene, the absence of which causes toxicity or enhances toxicity of the neurotoxic polypeptide. In the context of a huntingtin polypeptide expressed in a yeast system, the eukaryotic cell can lack, for example, the wild-type yeast gene apj1, apm2, aro9, ayr1, cit2, cmk1, cos111, cps1, dcg1, fil1, fpr2, gda1, glo2, gre2, gsh2, hlj1, hlr1, hms1, ipk1, kgd1, msb1, mrpl1, mup1, npt1, pcl6, phm8, prm5, psp1, rim4, sam2, sas3, sdt1, sip18, sng1, stp2, tea1, tvp15, ubp13, vps70, yhb1, yrb30, ybr100w, ybr258w, ydr215c, ygr015c, jlr107w, ykr017c, ykr064, ylr128w, ymr160w, ynl296w, yor292c, yor300w and/or ypl067c. In a related embodiment, the yeast strain can lack at least two, or at least three of these wild-type genes, the absence of which causes or enhances toxicity of the neurotoxic polypeptide.

In another embodiment in the context of a huntingtin polypeptide expressed in a yeast system, the yeast strain can lack, for example, apj1, apm2, ayr1, cit2, cmk1, cps1, fpr2, gda1, glo2, gre2, gsh2, hlj1, hms1, kgd1, msb1, mup1, rim4, sam2, sas3, stp2, ubp13, vps70, yhb1, ygr015c, ykr017c, ylr128w and/or yor292c. In a related embodiment, the yeast strain can lack at least two, or at least three of these wild-type genes, the absence of which causes or enhances toxicity of the neurotoxic polypeptide.

In other embodiments in the context of a huntingtin polypeptide, the eukaryotic cell of the eukaryotic cell expression system can lack, for example, an ortholog of at least one, at least two, or at least three of the yeast genes set forth above. For example, in a eukaryotic cell expression system, such as a rat, mouse, Drosophila, or C. elegans system, the eukaryotic cell can lack an ortholog of at least one of these wild-type genes, the absence of which causes or enhances toxicity of the neurotoxic polypeptide. In a related embodiment, the eukaryotic cell can lack, for example, at least one, at least two, or at least three orthologs of the following wild-type genes: DNAJA2, DNAJA1, DNAJB1, APIM1, AP1M2, AP2M1, HSD17B1, HSD17B2, RDH8, CS, CKLIK, CAMK1, CAMK1G, FLJ32569, ACY1, FKBP2, FKBP14, FKBP10, ENTPD6, ENTPD5, ENTPD3, HAGH, BRP17, MGC2605, HSD3B1, H105E3, GSS, MGC26226, DNAJA3, TFEB, SREBF1, MITF, OGDH, FLJ10851, KIAA1630, NCOA1, MGC20460, SLC7A9, SLC7A7, SLC7A6, HSU53209, SFRS10, TIAL1, MATLA, MAT2A, HTATIP, HBOA, RUNXBP2, LOC284459, LOC126295, OAZ, FLJ12552, USP12, USP10, FOLH1, NAALAD2, NGB, HBG1, WBSCR21, ARIH1, ARIH2, RP42, MGC2714, KIAA0276, MPV17, and/or PXMP2.

In another related embodiment in the context of a huntingtin polypeptide in which the cell expression system comprises ex vivo human cells, the cell can lack, for example, at least one, at least two, or at least three of the following wild-type genes: DNAJA2, DNAJA1, DNAJB1, AP1M1, AP1M2, AP2M1, HSD17B1, HSD17B2, RDH8, CS, CKLIK, CAMK1, CAMK1G, FLJ32569, ACY1, FKBP2, FKBP14, FKBP10, ENTPD6, ENTPD5, ENTPD3, HAGH, BRP17, MGC2605, HSD3B1, H105E3, GSS, MGC26226, DNAJA3, TFEB, SREBF1, MITF, OGDH, FLJ10851, KIAA1630, NCOA1, MGC20460, SLC7A9, SLC7A7, SLC7A6, HSU53209, SFRS10, TIAL1, MAT1A, MAT2A, HTATIP, HBOA, RUNXBP2, LOC284459, LOC126295, OAZ, FLJ12552, USP12, USP10, FOLH1, NAALAD2, NGB, HBG1, WBSCR21, ARIH1, ARIH2, RP42, MGC2714, KIAA0276, MPV17, and/or PXMP2.

In the context of an α-synuclein polypeptide expressed in a yeast system, the yeast cell can lack, for example, the wild-type yeast gene ape2, arl3, arol, cog6, crhl, cvt17, dpp1, fun26, gip2, glo4, gtt1, hbs1, hsp30, ino4, mad1, mal31, mei4, met17, met32, msb3, nbp2, nit2, nup53, opi3, pca1, pex2, pex8, pho13, pox1, ptk2, rpl41a, rny1, sac2, sap4, sod2, stf1, stp2, suv3, swr1, thi7, tlg2, thrl, tna1, tsl1, ubc8, vps24, vps28, vps60, war1, yat1, ybr013c, ybr284w, ybr300c, yc1042w, ycr026c, ycr050c, ycr051w, ycr085w, ydl118w, ydr154c, ydr220c, ygl109w, ygl165c, ygl226w, ygl231c, ygl262w, ygr130c, ygr154c, ygr201c, ygr290w, yhr199c, yjl118w, yjl122w, yjl135w, yjr154w, ykl098w, ykl100c, ykr023w, ykr035c, yrl365w, ylr376c, ymr226c, yml089c, ymr289w and/or yp136w. In a related embodiment, the yeast strain can lack at least two or at least three of these wild-type genes, the absence of which causes or enhances toxicity of the neurotoxic polypeptide.

In another embodiment in the context of an α-synuclein polypeptide, the eukaryotic cell can lack, for example, ape2, arl3, cog6, crhl, dpp1, fun26, gip2, glo4, hbs1, mal31, met17, met32, msb3, nbp2, nit2, nup53, opi3, pca1, pex2, pho13, pox1, ptk2, rny1, sac2, sod2, stp2, suv3, swr1, tlg2, tna1, ubc8, vps24, vps28, yat1, ybr284w, ycr026c, ycr051w, ygl231c, ygr130c, ygr201c, ykl100c, ykr023w, and/or ymr226c. In a related embodiment, the eukaryotic cell can lack at least two or at least three of these wild-type genes, the absence of which causes or enhances toxicity of the neurotoxic polypeptide.

In other embodiments in the context of an α-synuclein polypeptide, the eukaryotic cell of the expression system can lack, for example, an ortholog of one of at least one, at least two, or at least three of the yeast genes set forth above. For example, in a eukaryotic cell expression system, such as a rat, mouse, Drosophila, or C. elegans system, the eukaryotic cell can lack an ortholog of at least one of these wild-type genes, the absence of which causes or enhances toxicity of the neurotoxic polypeptide. In a related embodiment, the eukaryotic cell genetic can lack, for example, at least one, at least two, or at least three orthologs of the following wild-type genes: NPEPPS, ENPEP, LRAP, ARFRP1, FLJ22595, ARL5, COG6, MUC16, KIAA2026, MUC12, HTPAP, PPAP2A, PPAP2B, ENT3, SLC29A1, SLC29A2, PPPIR3c, PPP1R3B, PPP1R3A, HAGH, MR-1, MGC2605, HBS1L, GSPT2, GSPT1, SLC2A2, SLC2A14, SLC2A3, CTH, FLJ23436, ZNF214, ZNF132, TBC1D8, KIAA1055, EP164, SH3RF, SSH3BP1, SH3GL1, NIT1, NIT2, UPB1, LOC129401, PEMT, ATP7B, ATP7A, ATP12A, PXMP3, DJ37E16.5, ACOX1, ACOX2, ACOX3, SSTK, MARK2, STK22B, RNASE6PL, VPS52, SOD2, LOC284459, MGC43537, SUPV3L1, KIAA0052, DDX27, SRCAP, KIAA1259, EP400, STX16, STX1B2, STX1A, SLC17A5, C20ORF59, UBE2H, UBE2D3, UBE2A, NEDF, BC-2, DKFZP564O123, CPT2, CRAT, CHAT, AMPD2, AMPD1, AMPD3, ENPP5, ENPP3, ENPP1, TNKS2, TNKS, MIB, LOC51234, TGOLN2, RNF111, NEDL2, EEF1G, VARS2, HM13, SPPL2B, SPPL2A, TRIP4, RDH8, MGC417 and/or RETSDR2.

In a related embodiment in the context of an α-synuclein polypeptide in which the eukaryotic cell expression system comprises human cells, the eukaryotic cell can lack, for example, at least one, at least two, or at least three of the following wild-type genes: NPEPPS, ENPEP, LRAP, ARFRP1, FLJ22595, ARL5, COG6, MUC16, KIAA2026, MUC12, HTPAP, PPAP2A, PPAP2B, ENT3, SLC29A1, SLC29A2, PPPIR3c, PPPIR3B, PPP1R3A, HAGH, MR-1, MGC2605, HBSIL, GSPT2, GSPT1, SLC2A2, SLC2A14, SLC2A3, CTH, FLJ23436, ZNF214, ZNF132, TBC1D8, KIAA1055, EP164, SH3RF, SSH3BP1, SH3GL1, NIT1, NIT2, UPB1, LOC129401, PEMT, ATP7B, ATP7A, ATP12A, PXMP3, DJ37E16.5, ACOX1, ACOX2, ACOX3, SSTK, MARK2, STK22B, RNASE6PL, VPS52, SOD2, LOC284459, MGC43537, SUPV3L1, KIAA0052, DDX27, SRCAP, KIAA1259, EP400, STX16, STX1B2, STX1A, SLC17A5, C20ORF59, UBE2H, UBE2D3, UBE2A, NEDF, BC-2, DKFZP564O123, CPT2, CRAT, CHAT, AMPD2, AMPD1, AMPD3, ENPP5, ENPP3, ENPP1, TNKS2, TNKS, MIB, LOC51234, TGOLN2, RNF111, NEDL2, EEF1G, VARS2, HM13, SPPL2B, SPPL2A, TRIP4, RDH8, MGC417 and/or RETSDR2.

In certain embodiments according to the present invention, the wild-type gene is not a heat shock gene. For example, in certain embodiments, the wild-type gene does not encode Hsp40. In another embodiment, the wild-type gene does not encode Hsp70. In additional embodiments, the wild-type gene does not encode Hsp40, Hsp70 or a homolog thereof.

The eukaryotic cell expression system according to the present invention expresses a neurotoxic polypeptide. Typically, a nucleic acid encoding the neurotoxic polypeptide is introduced into at least one cell of the expression system. For example, a nucleic acid encoding a neurotoxic polypeptide can be introduced into a yeast cell. The nucleic acid can be introduced, for example, as a linear nucleic acid fragment, or as part of a replicating or integrating vector. The nucleic acid can encode a full-length, substantially full-length, or functionally equivalent form, of the neurotoxic polypeptide. Alternatively, the neurotoxic polypeptide can be a truncated polypeptide or a polypeptide with one or more internal deletions. The nucleic acid encoding the neurotoxic polypeptide is typically derived from a human source. In additional embodiments, the nucleic acid encoding the neurotoxic polypeptide can encode a non-human, mammalian homolog of the human neurotoxic polypeptide. In exemplary embodiments, the nucleic acid encoding a neurotoxic polypeptide encodes a human huntingtin or α-synuclein polypeptide, which can be introduced into the yeast cell by transformation.

As used herein, the term "nucleic acid" generally refers to at least one molecule or strand of DNA, RNA or a derivative or mimic thereof, comprising at least one base, such as, for example, a naturally occurring purine or pyrimidine base found in DNA (e.g., adenine "A," guanine "G," thymine "T," and cytosine "C") or RNA (e.g., A, G, uracil "U," and C). The term "nucleic acid" encompasses the terms "oligonucleotide" and "polynucleotide." The term "oligonucleotide" refers to at least one molecule of between about 3 and about 100 bases in length. The term "polynucleotide" refers to at least one molecule of greater than about 100 bases in length. These definitions generally refer to at least one single-stranded molecule, but in specific embodiments also encompass at least one additional strand that is partially, substantially or fully complementary to the at least one single-stranded molecule. Thus, a nucleic acid can encompass at least one double-stranded molecule that comprises one or more complementary strand(s) or "complement(s)" of a particular sequence comprising a strand of the molecule.

Nucleic acid can be obtained from any suitable source. Non-limiting examples of synthetic nucleic acid, particularly a synthetic oligonucleotide, include a nucleic acid made by in vitro chemical synthesis using phosphotriester, phosphite or phosphoramidite chemistry, by solid phase techniques such as described in EP 266,032, incorporated herein by reference, or by deoxynucleoside H-phosphonate intermediates. Enzymatically-produced nucleic acid can be made, for example, by amplification reactions, such as polymerase chain reaction (PCR) (see, e.g., U.S. Pat. Nos. 4,683,202 and 4,682,195, each incorporated herein by reference herein), or by the synthesis of oligonucleotides described in U.S. Pat. No. 5,645,897 (incorporated herein by reference). Biologically-produced nucleic acid include recombinant nucleic acid production in living cells, such as bacterial, yeast and human cells. (See generally Sambrook et al., *Molecular Cloning, A Laboratory Manual* (3rd ed. 2001); Ausubel et al. (eds.), *Current Protocols in Molecular Biology* (1994); Sambrook et al., *Molecular Cloning, A Laboratory Manual* (2nd ed. 1989), which are incorporated herein by reference.)

The term "gene" refers to a nucleic acid that is transcribed. As used herein, a "gene segment" is a nucleic acid segment of a gene. A gene can include regulatory sequences involved in transcription, or message production or composition. In particular embodiments, the gene comprises transcribed sequences that encode a protein, polypeptide or peptide. In keeping with the terminology described herein, an "isolated gene" can comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments can express, or can be adapted to express using nucleic acid manipulation technology, proteins, polypeptides, domains, peptides, fusion proteins, mutants and/or such like. Thus, a "truncated gene" refers to a nucleic acid sequence that is missing a stretch of contiguous nucleic acid residues that encode a portion of a full-length protein or polypeptide. For example, a truncated gene may not contain the nucleic acid sequence for the N-terminal region of the protein or polypeptide.

The nucleic acid encoding the neurotoxic polypeptide can be, for example, an expression construct. Expression constructs encoding a neurotoxic polypeptide can be prepared by recombinant nucleic acid technology. An expression construct can include, for example, at least one nucleic acid encoding the neurotoxic polypeptide. In certain embodiments, an expression construct can include all or a portion of the DNA sequences identified by Database Accession numbers: Genbank NM_000345 for alpha-synuclein; Genbank NT_006081, for the accession number for chromosome 4 where the Huntingtin gene is located; Genbank AX460946 and AX460944, for the accession numbers for mutant forms of the Huntingtin gene; and Genbank NM_002111 for the mRNA sequence expressed by the Huntingtin gene.

A nucleic acid encoding a neurotoxic polypeptide can be combined with other nucleic acid sequences, including but not limited to, one or more promoters, enhancers, polyadenylation signals, restriction enzyme sites, multiple cloning sites, coding segments, and the like, to create one or more expression construct(s) The overall length can vary considerably between expression constructs. Thus, a nucleic acid segment of almost any length can be employed, with the total length preferably being limited by the ease of preparation or use in the intended recombinant nucleic acid protocol.

The expression of the neurotoxic polypeptide is typically directed by a promoter. A "promoter" is a control sequence that controls the initiation and rate of transcription. It can contain genetic elements at which regulatory proteins and molecules bind, such as RNA polymerase and other transcription factors, to initiate the specific transcription of a nucleic acid sequence. A promoter can also include an enhancer. The phrases "operatively positioned," "operatively linked," and "operatively associated" mean that a promoter is in a correct functional location and/or orientation in relation to a nucleic acid sequence to control transcriptional initiation and/or expression of a downstream sequence.

A promoter can be naturally associated with a nucleic acid sequence, as can be obtained by isolating the 5' non-coding sequences located upstream of the coding segment and/or exon. Such a promoter can be referred to as "endogenous." Alternatively, the promoter can be "heterologous," from a different gene, or from a gene from a different species of organism. In some embodiments, expression of the neurotoxic polypeptide can be controlled by an inducible promoter, such as, for example, Gal1-10, Gal1, GalL, GalS, or CUP1 or a repressible promoter, such as Met25, for expression in yeast. (See generally Ausubel et al. (supra).) An expression construct can include at least one termination signal and/or polyadenylation signal, as needed.

Nucleic acids, such as expression constructs, can be introduced into cells of a eukaryotic cell expression system, such as a yeast cell, using a nucleic acid vector, including but not limited to, plasmids, linear nucleic acid molecules, artificial chromosomes and episomal vectors. Yeast plasmids, including integrating, centromere, autonomously replicating, and 2 micron vectors, are typically used for recombinant expression in yeast. Yeast plasmids typically include an antibiotic resistance gene, a bacterial origin of replication (for propagation in bacterial cells), and a selectable marker for maintenance in yeast cells. The yeast selectable marker is typically a nutritional gene (or "auxotrophic marker") such as, for example, TRP1, URA3, LEU2, HIS3 and/or LYS2.

Exemplary integrating vectors include YIp vectors, which are typically maintained in yeast by integration into the chromosomal DNA. Integrating vectors typically include a gene of interest (e.g., encoding the neurotoxic polypeptide), a bacterial origin of replication, and a selectable marker.

Exemplary centromere vectors include YCp and related plasmids, which typically contain an autonomous replicating sequence (e.g., ARS1), a centromere sequence (e.g., CEN4), a gene of interest (e.g., encoding the neurotoxic polypeptide), a bacterial origin of replication, and a selectable marker. Centromere plasmids are usually present at 1-2 copies per cell. Removal of the CEN sequence yields a replicative YRp plasmid, which is typically present in 100-200 copes per cell, and can be mitotically and meiotically unstable.

2 micron vectors contain a 2 micron sequence, which acts as a yeast replicon giving rise to higher plasmid copy number. The plasmid copy number can be increased by using a selectable marker operatively linked to a crippled promoter. This selectable marker is typically the LEU2 gene with a truncated promoter (LEU2-d), such that low levels of the Leu2p protein are produced. Examples of 2 micron vectors include YEp plasmids, such as YEp24 and the YEplac series of plasmids. (See, e.g., Sikorski, *Plasmid, A Practical Approach* (ed. K. G. Hardy), IRL Press (1993); and *Yeast Cloning Vectors and Genes, Current Protocols in Molecular Biology*, Section II, Unit 13.4, Eds., Ausubel et al. (1994).)

An expression construct can also be introduced into a cell of a eukaryotic cell expression system by homologous recombination. Yeast and other organisms perform homologous recombination such that a free end of a nucleic acid can recombine with a homologous nucleic acid in the cell, which results in insertion of the introduced nucleic acid into the chromosomal DNA.

In certain embodiments, the expression of the neurotoxic polypeptide can be increased to increase toxicity. Levels of the neurotoxic polypeptide can be increased, for example, by expressing a nucleic acid encoding the neurotoxic polypeptide using a "strong" promoter and/or increasing the copy number of the nucleic acid encoding the neurotoxic polypeptide. For example, strong constitutive and inducible yeast promoters include the promoters for the genes encoding elongation factor 1 (TEF1 and TEF2), alcohol dehydrogenase I (ADHI) promoter, the GAL1-GAL10 promoter, the CUP1 promoter, or the like. The copy number of the nucleic acid encoding the neurotoxic polypeptide can be increased, for example, by including it in a high copy number plasmid, such as a Yep or YRp plasmid.

The nucleic acid encoding the neurotoxic polypeptide can be introduced into cells of a eukaryotic cell expression system according to methods known to the skilled artisan. For example, yeast cells are typically transformed by chemical methods, such as the lithium acetate method (e.g., as described by Rose et al., *Methods in Yeast Genetics*, Cold Spring Harbor Laboratory Press, Cold Spring Harbor, N.Y. (1990)). Transformed cells are then isolated on selective media. Yeast cells transformed with a nucleic acid can be identified, for example, by including a marker in the expression vector. Methods of introducing nucleic acids into other eukaryotic cells are known in the art. (See, e.g., Sambrook et al. (supra); Ausubel et al. (supra).)

As will be appreciated by the skilled artisan, one or more homologs or orthologs of genes causing toxicity or enhanced toxicity of a neurotoxic polypeptide also can be expressed in the eukaryotic cell expression system using recombinant technology, as described herein or as known to the skilled artisan.

The eukaryotic cell expression system is used to screen candidate agents to identify those agents that reduce or ameliorate toxicity of the neurotoxic polypeptide. Without intending to be bound by any particular theory, candidate agents can, for example, reduce or prevent protein misfolding, aggregation, accumulation, localization and/or deposition (e.g., in inclusion bodies). Irrespective of the exact mechanism of action, a candidate agent identified by the screening methods according to the present invention can provide a therapeutic benefit to patients with neurodegenerative disease, or can be used as a lead compound to develop a therapeutic agent. A "therapeutic benefit" in the context of the present invention refers to anything that promotes or enhances the well-being of the subject with respect to the medical treatment of the subject's condition, which includes treatment of neurodegenerative disease, such as Huntington' and Parkinson's diseases. A list of nonexhaustive examples of this includes extension of the subject's life by any period of time, decrease or delay in the development of the disease, decrease in number of aggregation, plaques or fibrils, reduction in fibril growth, reduction in number of misfolded proteins, delay in onset of lapse in mental capabilities, and a decrease in atrophy, or dementia to the subject that can be attributed to the subject's condition.

The screening methods according to the present invention typically utilize a yeast expression system that expresses the neurotoxic polypeptide. As discussed above, the cells of the expression system also have a genetic background in which the neurotoxic polypeptide is toxic. The toxic phenotype is typically manifested by growth inhibition, growth arrest or cell death. For example, expression of the huntingtin fragment in a yeast cell having a suitable genetic background causes the yeast cell to be severely growth retarded or causes it to die when the huntingtin fragment is expressed. Contacting such a yeast cell with one or more ("at least one") candidate agent facilitates identification of one or more agents that can reduce the toxicity (also referred to as a "toxic phenotype"), such as by alleviating growth inhibition and/or cell death. Such an identified candidate agent may also reduce or prevent neurotoxicity of the neurotoxic polypeptide in humans (e.g., the accumulation of huntingtin protein in a human cell), thereby providing a method of identifying a potential therapeutic agent (or lead compound) for the development of a therapeutic agent for the treatment of humans having the neurodegenerative disease. Such a therapeutic agent may be used, for example, to prevent, treat and/or ameliorate the symptoms of Huntington's disease, Parkinson's disease, or the like.

As used herein, "candidate agent" refers to any agent with a potential to reduce, alleviate, prevent, or reverse the toxic effects of a neurotoxic polypeptides in the eukaryotic cell expression system. The term "potential therapeutic agent" refers to an agent that can reduce, alleviate, prevent, or reverse the toxic effects of a neurotoxic polypeptide in a cell, as determined, e.g., by the methods described herein. Potential therapeutic agents will be recognized as having the potential in vivo to reduce, alleviate, prevent, or reverse at least one symptom of a neurodegenerative disease associated with the neurotoxic polypeptide. A "potential therapeutic agent" as defined herein need not actually exhibit therapeutic efficacy in vivo: since candidate agents identified as having substantial activity on cells in vitro are useful, e.g., for the elucidation of structure-activity relationships associated with suppression of toxicity in cells, these agents can be used (e.g., as lead compounds) for the further development of a therapeutic agent that substantially retains the ability (or has an improved ability) to inhibit toxicity of the neurotoxic polypeptide in a cell, but which also has, relative to the originally identified agent, other properties better suited for in vivo use (e.g., increased stability, increased cellular uptake, or other properties which provide for a more favorable pharmacokinetic and/or pharmacodynamic profile).

Many types of candidate agents can be screened by the methods according to the present invention. Suitable candidate agents include, for example, small molecules, nucleic acids, peptides, peptidomimetics, synthetic compounds and/or natural compounds. A candidate agent can be contacted with the cell according to the characteristics of the candidate agent and the cell. A cell can be contacted with a nucleic acid by transformation. A cell also can be contacted with a candidate agent by culturing the cell in media containing the candidate agent. For example, a yeast cell can be contacted with a candidate agent by culturing the cell in liquid media, or growing the cell on solid or semi-solid media containing the candidate agent. In certain embodiments, the cell wall of a yeast cell can be partially removed to generate a spheroplast, and the spheroplast contacted with the candidate agent. The spheroplasts optionally can regenerate in the presence of the candidate agent. Similarly, insect and mammalian cells can be contacted with a candidate agent by including the agent in the culture media.

In an animal model system in which a neurotoxic polypeptide is expressed (e.g., an animal model for neurodegenerative disease), the cell can be contacted with the candidate agent by administering the candidate agent to the animal. For example, in certain embodiments in which the neurotoxic polypeptide is a huntingtin polypeptide comprising an expanded polyQ repeat, the candidate agent is administered to an animal model for Huntingtion's Disease. In other variations in which the neurotoxic polypeptide is an α-synuclein polypeptide, the candidate agent is administered to an animal model for Parkinson's Disease. Animal models for Huntington's Disease and Parkinson's Disease and which are useful in accordance with the present methods are well-known in the art. (See, e.g., Beal and Ferrante, *Nature Reviews* 5:373-384, 2004; Maries et al., *Nature Reviews* 4:727-738, 2004.) The candidate agent can be administered orally, intravenously, by infusion or injection, or the like. Candidate agents are administered to the animals either before or after the onset of disease symptoms using one or more treatment regimens (based on, e.g., administration routes, dosage, frequency of dosing, and the like), and the animals are monitored for amelioration of one or more disease symptoms.

Genetic agents can be screened by contacting the cell of the expression system with a nucleic acid encoding a gene or gene fragment. In a specific example, a genomic or cDNA library can be introduced into a yeast cell to identify a candidate agent that reduces the toxicity of the neurotoxic polypeptide. The library can be homologous or heterologous with respect to the cell expression system. For example, if the cell expression system is yeast, the library could from a non-yeast source, such as a human, mammalian or bacterial source.

In certain embodiments, the library optionally can be pre-screened or treated to reduce the number of copies of nucleic acids encoding the wild-type gene, or a homolog(s) thereof, which is lacking in the eukaryotic cell of the expression system. Thus, in certain embodiments, a candidate agent is identified which is a nucleic acid, provided that the candidate agent is not a nucleic acid containing the wild-type gene, and/or provided that the candidate agent is not a nucleic acid containing a homolog of the wild-type gene.

In other examples, cells of the expression system can be contacted with proteinaceous candidate agents, such as proteins, polypeptides and/or peptides. Suitable proteinaceous candidate agents that can be screened include homologous and heterologous proteins, including chaperones, hormones, growth factors, neurotransmitters, heat shock proteins, receptors, enzymes, ligands, regulatory factors, structural proteins and proteinaceous drugs. Candidate agents also can include, for example, nuclear proteins, cytoplasmic proteins, mitochondrial proteins, secreted proteins, membrane-associated proteins, serum proteins, viral proteins, bacterial proteins, protozoal proteins, and/or parasitic proteins. Candidate agents can additionally include proteinaceous materials such as unmodified proteins, polypeptide and/or peptides as well as lipoproteins, glycoproteins, phosphoproteins and nucleases.

In addition, cells of the expression system can be contacted with random and/or semi-random libraries of peptides and/or nucleic acids. In related embodiments, cells of the expression system can be contacted with peptidomimetics. The term "peptidomimetic" refers to a synthetic chemical compound that has substantially the same structural and functional characteristics as a protein, polypeptide or peptide. Peptide analogs are commonly used in the pharmaceutical industry as non-peptide drugs with properties analogous to those of the template peptide. These types of non-peptide compounds are termed "peptide mimetics" or "peptidomimetics" (see, e.g., Fauchere, *J. Adv. Drug Res.* 15:29 (1986); Veber and Freidinger *TINS* p. 392 (1985); and Evans et al., *J. Med. Chem.* 30:1229 (1987); which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (e.g., a polypeptide that has a desired biological or pharmacological activity), but have one or more peptide linkages optionally replaced by a linkage selected from the group consisting of, e.g., —$CH_2NH$—, —$CH_2S$—, —$CH_2$—$CH_2$—, —CH=CH—(cis and trans), —$COCH_2$—, —CH(OH)$CH_2$—, and —$CH_2SO$—. The mimetic can be either entirely composed of synthetic, non-natural analogues of amino acids, or, is a chimeric molecule of partly natural peptide amino acids and partly non-natural analogs of amino acids. The mimetic can also incorporate natural amino acid conservative substitutions as long as such substitutions also do not substantially alter the mimetic's structure and/or activity.

Candidate agents also can be from libraries of synthetic and/or natural compounds. One example is a library of FDA-approved compounds that can be used by humans. In addition, synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.), and a rare chemical library is available from Aldrich (Milwaukee, Wis.).

Combinatorial libraries are available and/or can be prepared. Alternatively, libraries of natural compounds in the form of bacterial, fungal, plant and animal extracts are also available, for example, from Pan Laboratories (Bothell, Wash.) or MycoSearch (N.C.), or can be prepared. Compounds isolated from natural sources, such as animals, bacteria, fungi, plant sources, including leaves and bark, and marine samples also can be screened as candidate agents.

Other suitable candidate agents include antisense molecules, ribozymes, and antibodies (including single chain antibodies and Fv fragments). For example, an antisense molecule that binds to a translational or transcriptional start site, or a splice junction, can be a candidate agent. Additionally, natural and synthetically-produced libraries and compounds are readily modified through conventional chemical, physical, and biochemical means.

Screening of such libraries, including combinatorially generated libraries (e.g., peptide libraries) can be performed in a rapid and efficient way to screen a large number of related and/or unrelated compounds. Combinatorial approaches also lend themselves to rapid evolution of potential therapeutic agents by the creation of second, third and fourth generation compounds modeled on active, but otherwise undesirable compounds.

Candidate agents can be found within compounds of numerous chemical classes, though typically they are organic compounds, and can include small organic compounds. Small organic compounds have a molecular weight of more than 50 yet less than about 2,500 daltons, typically less than about 750, or less than about 350 daltons. Exemplary classes include heterocycles, peptides, saccharides, steroids, triterpenoid compounds, or the like. Structural identification of an agent can be used to identify, generate, or screen additional candidate agents. For example, where peptide agents are identified, they can be modified in a variety of ways to enhance their stability, such as using an unnatural amino acid, such as a D-amino acid, by functionalizing the amino or carboxylic terminus (e.g., for the amino group, acylation or alkylation, and for the carboxyl group, esterification or amidification), or the like.

Preparation and screening of combinatorial chemical libraries is well known to those of skill in the art. Such combinatorial chemical libraries include, but are not limited to, peptide libraries (see, e.g., U.S. Pat. No. 5,010,175; Furka, *Int. J. Pept. Prot. Res.* 37:487-93 (1991); and Houghton et al., *Nature* 354:84-88 (1991)). Other chemistries for generating chemical diversity libraries also can be used. Such chemistries include, but are not limited to: peptoids (see, e.g., PCT Publication No. WO 91/19735), encoded peptides (see, e.g., PCT Publication WO 93/20242), random bio-oligomers (see, e.g., PCT Publication No. WO 92/00091), benzodiazepines (see, e.g., U.S. Pat. No. 5,288,514; and Baum, *C&EN*, Jan. 18, 1993, p. 33), diversomers such as hydantoins, benzodiazepines and dipeptides (see, e.g., Hobbs et al., *Proc. Nat. Acad. Sci. USA* 90:6909-13 (1993)), vinylogous polypeptides (see, e.g., Hagihara et al., *J. Amer. Chem. Soc.* 114:6568 (1992)), nonpeptidal peptidomimetics with glucose scaffolding (see, e.g., Hirschmann et al., *J. Amer. Chem. Soc.* 114:9217-18 (1992)), analogous organic syntheses of small compound libraries (see, e.g., Chen et al., *J. Amer. Chem. Soc.* 116:2661 (1994)), oligocarbamates (see, e.g., Cho et al., *Science* 261: 1303 (1993)), peptidyl phosphonates (see, e.g., Campbell et al., *J. Org. Chem.* 59:658 (1994)), nucleic acid libraries (see, e.g., Ausubel et al. (supra), and Sambrook, (supra)), peptide nucleic acid libraries (see, e.g., U.S. Pat. No. 5,539,083), antibody libraries (see, e.g., Vaughn et al., *Nature Biotechnology*, 14(3):309-14 (1996) and PCT/US96/10287), carbohydrate libraries (see, e.g., Liang et al., *Science* 274:1520-22 (1996) and U.S. Pat. No. 5,593,853), small organic molecule libraries, such as isoprenoids (see, e.g., U.S. Pat. No. 5,569, 588), thiazolidinones and metathiazanones (see, e.g., U.S. Pat. No. 5,549,974), pyrrolidines (see, e.g., U.S. Pat. Nos. 5,525,735 and 5,519,134), morpholino compounds (see, e.g., U.S. Pat. No. 5,506,337), or the like.

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif; 9050 Plus, Millipore, Bedford, Mass.). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences, Columbia, Md.; etc.).

In other embodiments, yeast cells expressing a neurotoxic polypeptide in a suitable genetic background can be screened to identify secondary mutations in other yeast genes that reduce or alleviate the toxic effects of the polypeptide. Such yeast cells can be screened, for example, by transforming yeast cells of the expression system with a library of mutagenized genes (e.g., a mutagenized library of yeast chromosomal DNA or a library of mutagenized non-yeast DNA). In a related embodiment, yeast cells can be transformed with nucleic acids encoding null or mutant alleles of yeast genes, which can integrate by homologous recombination at the locus of the endogenous yeast genes.

Yeast cells expressing a neurotoxic polypeptide can be crossed to tester yeast cells of suitable mating type and which contain a mutant yeast gene(s). Such tester yeast cells may optionally also lacking the wild-type gene(s), the absence of expression of the wild-type causes or enhances toxicity of the neurotoxic polypeptide. The tester yeast cells also contain a mutation in a second mutant gene. Such a mutant gene can be, for example, a null allele, a deletion (e.g., strains of the yeast gene deletion set, see infra), or the gene can contain one or more nonsense, missense or frameshift mutations. Following mating, the mated yeast cells or their progeny can be screened to determine whether the additional mutant gene can alleviate the toxic effect of the neurotoxic polypeptide. In addition or alternatively, the mated yeast cells can be sporulated and the resulting progeny cells examined to determine if the "double mutant" (e.g., the mutation causing a lack of expression of the wild-type gene that causes or enhances toxicity of the neurotoxic polypeptide, and the second mutant gene) rescues the toxic phenotype of the yeast cells expressing the neurotoxic polypeptide in the suitable genetic background. In such a cross, the segregation of the nucleic acid encoding the neurotoxic polypeptide, the mutation associated with the genetic background (i.e., the absence of expression of the wild-type gene) and/or the additional mutant gene optionally can be followed by a suitable marker(s). Suitable markers can be, for example, the yeast URA3, TRP1, LEU2, or the like, or can be a suitable, genetically linked chromosomal marker.

Candidate agents that are initially identified by any of the foregoing screening methods can be further tested to validate the apparent activity. Typically, such studies are conducted by re-screening the agents. Alternatively, if a candidate agent is identified in one eukaryotic cell expression system (e.g., a yeast expression system), the identified candidate agent can be further characterized in another model system, such as a rat, mouse, *Drosophila* or *C. elegans* system, or cells isolated from such an organism or ex vivo human cells. Subsequent validation also can be performed with suitable animal models. The basic format of such methods can involve administering a lead compound identified during an initial screen to an animal that serves as a model for the human neurodegenerative disease and then determining if neurotoxicity is modulated. The animal models utilized in validation studies generally are mammals of any kind. Specific examples of suitable animals include, but are not limited to, primates, mice and rats.

In another aspect, methods are provided to identify mutations in genes that are correlated with neurodegenerative disease. Such screening methods can be performed by analyzing the sequences of genes for which the absence of wild-type function causes toxicity or enhances toxicity of a neurotoxic polypeptide. For example, one or more such human genes can be screened to identify mutations in genes that are associated with neurodegenerative disease. For example, the sequences of one more of the following genes can be screened in samples from subjects having or at risk for developing Huntington's disease: DNAJA2, DNAJA1, DNAJB1, AP1M1, AP1M2, AP2M1, HSD17B1, HSD17B2, RDH8, CS, CKLIK, CAMK1, CAMK1G, FLJ32569, ACY1, FKBP2, FKBP14, FKBP10, ENTPD6, ENTPD5, ENTPD3, HAGH, BRP17, MGC2605, HSD3B1, H105E3, GSS, MGC26226, DNAJA3, TFEB, SREBF1, MITF, OGDH, FLJ10851, KIAA1630, NCOA1, MGC20460, SLC7A9, SLC7A7, SLC7A6, HSU53209, SFRS10, TIAL1, MAT1A, MAT2A, HTATIP, HBOA, RUNXBP2, LOC284459, LOC126295, OAZ, FLJ12552, USP12, USP10, FOLH1, NAALAD2, NGB, HBG1, WBSCR21, ARIH1, ARIH2, RP42, MGC2714, KIAA0276, MPV17, and/or PXMP2.

Similarly, the sequences of one more of the following genes can be screened in samples from subjects having or at risk for developing Parkinson's disease: NPEPPS, ENPEP, LRAP, ARFRP1, FLJ22595, ARL5, COG6, MUC16, KIAA2026, MUC12, HTPAP, PPAP2A, PPAP2B, ENT3, SLC29A1, SLC29A2, PPP1R3c, PPP1R3B, PPP1R3A, HAGH, MR-1, MGC2605, HBS1L, GSPT2, GSPT1, SLC2A2, SLC2A14, SLC2A3, CTH, FLJ23436, ZNF214, ZNF132, TBC1D8, KLAA1055, EP164, SH3RF, SSH3BP1, SH3GL1, NIT1, NIT2, UPB1, LOC129401, PEMT, ATP7B, ATP7A, ATP12A, PXMP3, DJ37E16.5, ACOX1, ACOX2, ACOX3, SSTK, MARK2, STK22B, RNASE6PL, VPS52, SOD2, LOC284459, MGC43537, SUPV3L1, KIAA0052, DDX27, SRCAP, KIAA1259, EP400, STX16, STX1B2, STX1A, SLC17A5, C20ORF59, UBE2H, UBE2D3, UBE2A, NEDF, BC-2, DKFZP564O123, CPT2, CRAT, CHAT, AMPD2, AMPD1, AMPD3, ENPP5, ENPP3, ENPP1, TNKS2, TNKS, MIB, LOC51234, TGOLN2, RNF111, NEDL2, EEF1G, VARS2, HM13, SPPL2B, SPPL2A, TRIP4, RDH8, MGC417 and/or RETSDR2.

Typically, the methods comprise analyzing a nucleic acid of one or more of the above genes wild-type gene from subjects having, or at risk for developing a neurodegenerative disease. The sequence of a nucleic acid is analyzed to determine whether it contains a mutation, as compared with a nucleic acid from a wild-type nucleic acid. Such a mutation can be one or more nucleotide changes, deletions or insertions.

The sequence of the wild-type gene can be obtained from a reference library, from a healthy individual, or from a collection of individuals known not to have or to be at risk for developing the neurodegenerative disorder. The sequence of the wild-type gene also can be obtained from, for example, a sequence resulting from the Human Genome Project or a commercially available database containing such information.

Mutations in a gene can be detected by any suitable means for analyzing the sequence of a nucleic acid. For example, mutations can be detected by DNA sequence analysis, restriction fragment length polymorphism (RFLP) analysis, single-stranded length polymorphism (SSCP) analysis, allele-specific PCR, and the like. (See generally Sambrook et al., Ausubel et al., and Sambrook et al., all supra). Southern blot of genomic DNA (e.g., from a human) can be used for screening for a restriction fragment length polymorphism (RFLP) to detect the presence of a mutation associated with a neurodegenerative disorder.

In another embodiment, single nucleotide polymorphism (SNP) analysis can be used. Various real-time PCR methods including, e.g., Taqman or molecular beacon-based assays (see, e.g., U.S. Pat. Nos. 5,210,015 and 5,487,972; Tyagi et al., *Nature Biotechnology* 14:303 (1996); and PCT WO 95/13399) are useful to detect the presence or absence of a SNP. Other methods include ligase chain reaction (LCR) systems, and the nucleic acid sequence based amplification (NASBA, Cangene, Mississauga, Ontario) and Q Beta Replicase systems. These systems can be used to directly identify mutations where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman and molecular beacon probes can be used to monitor amplification reaction products, e.g., in real time.

Additional SNP detection methods include, for example, sequencing by nucleic acid hybridization, dot blotting, oligonucleotide array (DNA Chip) hybridization analysis, as described in, for example, e.g., U.S. Pat. No. 6,177,249; Landegren et al., *Genome Research* 8:769-76 (1998); Botstein et al., *Am. J. Human Genetics* 32:314-31 (1980); Meyers et al., *Methods in Enzymology* 155:501-27 (1987); Keen et al., Trends in Genetics 7:5 (1991); Myers et al., Science 230: 1242-46 (1985); and Kwok et al., Genomics 23:138-44 (1994).

In a typical embodiment, the methods comprise obtaining a biological sample, containing a nucleic acid containing a gene of interest, from a subject having or at risk for developing a neurodegenerative disease, and analyzing the nucleic acid to determine whether the gene of interest contains a mutation, as compared with a corresponding wild-type nucleic. The sample can be, for example, a tissue sample, blood sample, or other sample containing nucleic acids of the subject.

The nucleic acids in the sample can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild-type specific nucleic acid probe or PCR primers can serve as a negative probe in an assay sample where only the nucleotide sequence of interest is present.

In a related aspect, methods of analyzing the expression of one or more genes causing toxicity or enhanced toxicity of a neurotoxic polypeptide are provided. Those of skill in the art will recognize that the detection of differences in expression of such genes has many uses. For example, as discussed herein, detection of message levels from such genes can be useful for identifying changes in gene activity associated with neurodegenerative disease or a predisposition to a neurodegenerative disease. Moreover, detection of changes in gene expression can be useful to identify modulators of gene expression and/or neurotoxic polypeptide expression.

A variety of methods for specific DNA and/or RNA measurement that use nucleic acid hybridization techniques are known to those of skill in the art (see, e.g., Sambrook et al., Ausubel et al., and Sambrook et al., all supra). Some methods involve an electrophoretic separation (e.g., Southern blot for detecting DNA, and Northern blot for detecting RNA). Measurement of DNA and RNA can also be carried out in the absence of electrophoretic separation (e.g., by dot blot).

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins (*Nucleic Acid Hybridization, A Practical Approach*, IRL Press (1985)), Gall and Pardue (*Proc. Natl. Acad. Sci. USA* 63:378-383 (1969)), and John et al. (*Nature* 223:582-87 (1969)).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label can also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tjissen, "Practice and Theory of Enzyme Immunoassays," *Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex can later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids can be labeled by any one of several methods typically used to detect the presence of hybridized polynucleotides. Typical methods of detection use autoradiography with $^{3}H$, $^{125}I$, $^{35}S$, $^{14}C$, or $^{32}P$-labeled probes or the like.

Other labels include, for example, ligands that bind to labeled antibodies, fluorophores, chemiluminescent agents, enzymes, and antibodies that can serve as specific binding pair members for a labeled ligand. An introduction to labels, labeling procedures and detection of labels is found in Polak and Van Noorden, *Introduction to Immunocytochemistry*, 2nd ed. (Springer Verlag, New York (1997)); and in Haugland, *Handbook of Fluorescent Probes and Research Chemicals*, a combined handbook and catalogue published by Molecular Probes, Inc. (1996).

In general, a detector that monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of sources. Commonly, an optical image of a substrate comprising bound labeling moieties is digitized for subsequent computer analysis.

Most typically, the amount of, for example, RNA from a gene is measured by quantitating the amount of label fixed to the solid support by binding of the detection reagent. Typically, the presence of a modulator during incubation will increase or decrease the amount of label fixed to the solid support relative to a control incubation that does not comprise the modulator, or as compared to a baseline established for a particular reaction type. Means of detecting and quantitating labels are well known to those of skill in the art.

In some embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques can also be used. For instance, very large scale immobilized polymer arrays (VLSIPS™), e.g., Gene Chips or microarrays, available from Affymetrix, Inc. in Santa Clara, Calif. can be used to detect changes in expression levels of a plurality of genes involved in the same regulatory pathways simultaneously. (See Tijssen, supra.; Fodor et al., *Science* 251:767-77 (1991); Sheldon et al., *Clinical Chemistry* 39(4):718-19 (1993), and Kozal et al., *Nature Medicine* 2(7):753-59 (1996).) Similarly, spotted cDNA arrays (arrays of cDNA sequences bound to nylon, glass or another solid support) can also be used to monitor expression of a plurality of genes.

Typically, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition. (See, e.g., Schena et al., *Science* 270:467-70 (1995) and Lockhart et al., *Nature Biotech.* 14:1675-80 (1996).)

Hybridization specificity can be evaluated by comparing the hybridization of specificity-control polynucleotide sequences to specificity-control polynucleotide probes that are added to a sample in a known amount. The specificity-control target polynucleotides can have one or more sequence mismatches compared with the corresponding polynucleotide sequences. In this manner, whether only complementary target polynucleotides are hybridizing to the polynucleotide sequences or whether mismatched hybrid duplexes are forming is determined.

Hybridization reactions can be performed in absolute or differential hybridization formats. In the absolute hybridization format, polynucleotide probes from one sample are hybridized to the sequences in a microarray format and signals detected after hybridization complex formation correlate to polynucleotide probe levels in a sample. In the differential hybridization format, the differential expression of a set of genes in two biological samples is analyzed. For differential hybridization, polynucleotide probes from both biological samples (e.g., a control and a sample from a subject) are prepared and labeled with different labeling moieties. A mixture of the two labeled polynucleotide probes is added to a microarray. The microarray is then examined under conditions in which the emissions from the two different labels are individually detectable. Sequences in the microarray that are hybridized to substantially equal numbers of polynucleotide probes derived from both biological samples give a distinct combined fluorescence (see, e.g., PCT publication WO95/35505). In some embodiments, the labels are fluorescent labels with distinguishable emission spectra, such as, for example, Cy3 and Cy5 fluorophores.

After hybridization, the microarray is washed to remove nonhybridized nucleic acids and complex formation between the hybridizable array elements and the polynucleotide probes is detected. Methods for detecting complex formation are well known to those skilled in the art. In some embodiments, the polynucleotide probes are labeled with a fluorescent label and measurement of levels and patterns of fluorescence indicative of complex formation is accomplished by fluorescence microscopy, such as confocal fluorescence microscopy.

In a differential hybridization experiment, polynucleotide probes from two or more different biological samples are labeled with two or more different fluorescent labels with different emission wavelengths. Fluorescent signals are detected separately with different photomultipliers set to detect specific wavelengths. The relative abundances/expression levels of the polynucleotide probes in two or more samples are obtained.

Typically, microarray fluorescence intensities can be normalized to take into account variations in hybridization intensities when more than one microarray is used under similar test conditions. In some embodiments, individual polynucleotide probe/target complex hybridization intensities are normalized using the intensities derived from internal normalization controls contained on each microarray.

Detection of nucleic acids can also be accomplished, for example, by using a labeled detection moiety that binds specifically to duplex nucleic acids (e.g., an antibody that is specific for RNA-DNA duplexes). One example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Another example uses antibodies to RNA duplexes, including homo and heteroduplexes. (See, e.g., Coutlee et al., *Analytical Biochemistry* 181:153-62 (1989); Bogulavski et al., *J. Immunol. Methods* 89:123-30 (1986); Prooijen-Knegt, *Exp. Cell Res.* 141:397-407 (1982); Rudkin, *Nature* 265:472-73 (1976); Stollar, *Proc. Natl. Acad. Sci. USA* 65:993-1000 (1970); Ballard, *Mol. Immunol.* 19:793-99 (1982); Pisetsky and Caster, *Mol. Immunol.* 19:645-50 (1982); Viscidi et al., *J. Clin. Microbial.* 41:199-209 (1988); and Kiney et al., *J. Clin. Microbiol.* 27:6-12 (1989).) Kits comprising antibodies specific for DNA:RNA hybrids are available, for example, from Digene Diagnostics, Inc. (Beltsville, Md.).

In addition to available antibodies, one of skill in the art can make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (ed), *Fundamental Immunology*, Third Edition, Raven Press, Ltd., NY (1993); Coligan, *Current Protocols in Immunology*, Wiley/Greene, New York (1991); Harlow and Lane, *Antibodies: A Laboratory Manual*, Cold Spring Harbor Press, New York (1989); Stites et al. (eds.), *Basic and Clinical Immunology*, Fourth ed., Lange Medical Publications, Los Altos, Calif., and references cited therein; Goding, *Monoclonal Antibodies: Principles and Practice*, 2d ed., Academic Press, New York, N.Y. (1986); and Kohler and Milstein, *Nature* 256:495-97 (1975)). Other suitable techniques for antibody preparation include selection of libraries of recombinant antibodies in phage or similar vectors (see, e.g., Huse et al., *Science* 246:1275-81 (1989); and Ward et al., *Nature* 341:544-46 (1989)). Specific monoclonal and polyclonal antibodies and antisera will usually bind with a $K_D$ of at least about 0.1 μM, typically at least about 0.01 μM or better, and most typically and preferably, 0.001 μM or better.

An alternative means for determining the level of expression of the nucleic acids of the present invention is in situ hybridization. In situ hybridization assays are well known. (See, e.g., Angerer et al., *Methods Enzymol.* 152:649-60 (1987).) In an in situ hybridization assay, cells, typically human cells from the brain, are fixed to a solid support, typically a glass slide. If DNA is to be probed, the cells are denatured with heat or alkali. The cells are then contacted with a hybridization solution at a moderate temperature to permit annealing of specific probes that are labeled. The probes are typically labeled with radioisotopes or fluorescent reporters.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

The following examples are offered to illustrate, but not to limit the claimed invention.

Example 1

The baker's yeast *Saccharomyces cerevisiae* was used as a model eukaryotic organism to identify the targets and molecular mechanisms by which α-synuclein and a mutant huntingtin fragment mediate toxicity. This yeast is well studied because its basic cellular mechanisms, such as replication, recombination, cell division, protein folding, intracellular transport and metabolism, are similar to higher eukaryotes, including mammals. In addition, this yeast provides a model system for studies relating to basic mechanisms of protein misfolding, aggregation and toxicity. Similar to neurons, yeast transformed with mutant huntingtin fragments form inclusion bodies by a process also regulated by yeast homologs of Hsp40 and Hsp70 (Krobitsch et al., *Proc. Natl. Acad. Sci. USA* 97:1589-94 (2000); Muchowski et al., *Proc. Natl. Acad. Sci. USA* 97:7841-46 (2000)). As in many types of mammalian cells, over-expression of mutant huntingtin fragments in yeast has no effect on cell viability. This feature allows genetic screens to be performed to identify genes that unmask, or are required for, suppression of, toxicity.

These studies take advantage of a collection of gene deletion mutants of *S. cerevisiae*, developed by the *Saccharomyces* Genome Deletion Project (see Giaever et al., *Nature* 418: 387-91 (2002); Winzoler et al., *Science* 285:901-06 (1999)). Each yeast mutant in this collection lacks a single wild-type yeast gene. This collection has been used to identify new genes pathways involved in tolerance to radiation (Birrell et al., *Proc. Natl. Acad. Sci. USA* 98:12608-13 (2001)) and in human mitochondrial disease (Steinmetz et al., *Nat. Genet.* 31:400-04 (2002)), as well as to characterize the effects of pharmacological agents (Chan et al., *Proc. Natl. Acad. Sci. USA* 97:13227-32 (2000)). The yeast gene deletion set (YGDS) of 4,850 viable mutant haploid strains was screened to identify genes that modulate toxicity of α-synuclein or the mutant huntingtin fragment.

Methods and Materials

Yeast screening methods. The yeast gene deletion set (YGDS) was obtained from Research Genetics (Huntsville, Ala.) as a collection of 4,850 MATa (BY4741) haploid yeast strains frozen in glycerol stocks in 96-well microtiter dishes. These strains were thawed and inoculated individually into yeast extract/peptone/dextrose (YPD) liquid cultures in 96-well microtiter dishes using a Beckman Biomeck 2000 robot, grown to late stationary phase, and then grouped into 4 pools, each containing approximately 1200 strains. pSAL4-HD53Q (2 µm ori), expressing a huntingtin fragment (exon 1 of the huntingtin gene with a normal (HD20Q) and expanded (HD53Q) polyQ repeat under control of the CUP1 promoter; Muchowski et al., *Proc. Natl. Acad. Sci. USA* 99:727-32 (2002)), or pRS426GAL-α-synuclein (2 µm ori), expressing α-synuclein under the control of the Gal promoter was used to transform the pooled deletion strains using the lithium acetate method (Guthrie (ed.), *Guide to Yeast Genetics and Molecular Biology, Methods in Enzymology*, vol. 194 (1991)). For each construct and pool, approximately 18,000 individual transformants were observed (approximately 15 fold coverage) after plating onto 30 large agar plates that contained synthetic complete media lacking uracil (SC-Ura) to select transformants containing the plasmid. Screening this high number of transformants was done to ensure that every deletion strain within the pool was transformed and would be screened multiple times. As a control, the yeast cells were transformed with a control plasmid (e.g., pSAL4 orp426GAL), which lacked both a nucleic acid encoding the huntingtin fragment and α-synuclein.

Transformants from each pool were replica plated onto 30 plates containing SC-Ura+copper, or SC-Ura+galactose to induce the expression of HD53Q or α-synuclein, respectively. Plates were analyzed after 3 days of incubation at 30° C. For the HD53Q screen, colonies that grew in the absence of copper but appeared to die in its presence (335 colonies out of 60,000 transformants) were selected for further analysis. Each positive colony was first streaked onto a master plate that contained YPD. From each master plate, at least three independent colonies were re-streaked onto fresh SC-URA −/+copper plates to identify potential false positives. After re-testing, 68 colonies (20%) exhibited synthetic sickness or lethality in a reproducible manner. For the α-synuclein screen, colonies that grew on glucose but died on galactose (254 colonies out of approximately 60,000 transformants) were selected for further analysis. After re-testing to identify false positives (similar to that described above), 107 colonies (42%) exhibited synthetic sickness or lethality in a reproducible manner.

Identification of yeast gene deletion strains that are synthetically sick or lethal with HD53Q or α synuclein. Colony PCR was used to amplify a DNA sequence that contains a 20 base pair bar code that uniquely identifies each YGDS deletion strain. The amplified PCR product was subjected to a DNA sequencing reaction, the results of which were used in a BLAST search against a database located on the yeast gene deletion web page The results from BLAST searches revealed the identities of the individual deletion strains. The final number unique gene deletion strains sensitive to HD53Q or α synuclein decreased slightly because several strains were represented multiple times in the original set of positives (indicating the screen had been saturated), and due to the loss of three strains to copper or galactose sensitivity (see below). Each of the strains in the final collection of mutants were freshly streaked out from the original glycerol stocks in 96-well microtiter plates and re-transformed with the HD53Q- or a synuclein-expressing plasmids for subsequent analyses.

Analysis of viability in yeast gene deletion strains expressing with HD53Q or α-synuclein. Cell viability of the transformed YGDS strains was determined by serially diluting log phase cultures onto solid media as described previously (Muchowski et al., *Proc. Natl. Acad. Sci. USA* 99:727-32 (2002)). Briefly, for HD53Q, yeast cells transformed with empty vector (pSAL4), HD20Q or HD53Q were grown in liquid synthetic complete medium lacking uracil (SC-URA) to log-phase and then induced for 24 hours in SC-URA+copper. Aliquots containing an equal number of cells were removed from liquid cultures before (T=0) and after (T=24 hrs) copper induction were spotted on plates containing SC-URA −/+400 µM copper. The plates were incubated at 30° C. for three days. For α-synuclein, yeast cells transformed with empty vector (p426GAL) or α-synuclein-expressing plasmid were grown in liquid synthetic complete medium lacking uracil (SC-URA+glucose) to log-phase and then induced for six hours in SC-URA+galactose. Aliquots of cells containing equal numbers of cells were removed from liquid cultures before (T=0) and after (T=6 hrs) galactose induction, were spotted on plates containing SC-URA −/+galactose. The plates were incubated at 30° C. for three days.

For the HD53Q cell viability screen, two deletion strains out of the original 68 that were isolated (cup2Δ and pmr1Δ) exhibited copper sensitivity and were not analyzed further. One strain obtained from the α-synuclein screen was sensitive to galactose (gal7Δ) and likewise, was not further analyzed.

Suppression of HD53Q synthetic sickness or lethality in yeast gene deletion strains by human orthologs. cDNAs encoding full length clones of the human orthologs (USP12, ZNFN1A4, DNAJA2) of the yeast genes UBP13, STP2 and HLJ1 were PCR amplified from human brain cDNA and inserted into the pYES2 yeast expression vector, which uses a galactose-regulated promoter for expression. DNA sequencing analysis confirmed that the coding sequences of the orthologs were amplified correctly and inserted in the proper orientation for expression. Constructs that expressed the orthologs (or the empty vector, as a control) were co-transformed with plasmids expressing HD53Q into selected yeast gene deletion strains (i.e., lacking yeast genes UBP13, STP2 or HLJ1). Single transformants were streaked on SC-URA-TRP −/+copper/galactose and analyzed for viability under non-inducing and inducing conditions.

Results

In this model of huntingtin aggregation and inclusion body formation in S. cerevisiae, YGDS strains were transformed with constructs that express a huntingtin fragment (exon 1 of the huntingtin gene with a normal (HD20Q) and expanded (HD53Q) polyQ repeat) or α-synuclein. Previous studies indicate that the aggregation and inclusion body forming properties of huntingtin fragments with expanded polyQ tracts can be reproduced faithfully in S. cerevisiae (Muchowski et al., Proc. Natl. Acad. Sci. USA 97:7841-46 (2000)). Similarly, over-expression of wild-type or mutant (AS3T) human α-synuclein in yeast results in the formation of cytoplasmic inclusion bodies that, at the level of light microscopy, are similar to those formed by mutant huntingtin fragments in yeast.

To identify downstream targets and molecular mechanisms by which the mutant huntingtin fragment or α-synuclein mediate toxicity, genome-wide synthetic lethal screens were performed in yeast. A collection of 4,850 yeast strains was transformed with constructs that express the mutant huntingtin fragment or α-synuclein under the control of an inducible promoter. The transformants were plated onto selective media in the absence of induction. Transformants that were sensitive to the mutant huntingtin fragment or α-synuclein were identified by replica plating onto media that contained the appropriate inducer of protein expression (copper for the huntingtin construct and galactose for α-synuclein). Isolated colonies of the putative huntingtin or α-synuclein-sensitive mutants were re-tested in spotting assays that measured cell viability. Although positive colonies were selected originally because of their complete lack of growth (referred to as synthetic lethality) in the presence of copper or galactose, these subsequent tests indicated that a sub-lethal effect on toxicity (synthetic sickness) occurred in many of the deletion strains. Of 4850 mutants, 52 (approximately 1%) were identified with enhanced toxicity to the mutant huntingtin fragment (with an expanded polyQ repeat, HD53Q)), and 86 (approximately 2%) were identified with enhanced toxicity to wild-type α-synuclein (Tables 1 and 2).

TABLE 1

Yeast strains synthetically sick or lethal with huntingtin polypeptide expression.

| Yeast Gene Deletion | Human Ortholog | Function or Proposed Function |
|---|---|---|
| 1. apj1 | Yes | Hsp40 chaperone |
| 2. apm2 | Yes | non-selective vesicle transport |
| 3. ayr1 | Yes | ketoreductase:acylglycerone-phosphate reductase |
| 4. cit2 | Yes | citrate synthase, peroxisomal |
| 5. cmk1 | Yes | protein histidine kinase |
| 6. cos111 | No | possibly involved in ubiquitin pathway |
| 7. cps1 | Yes | gly-X carboxypeptidase |
| 8. dcg1 | No | possibly involved in cell wall biosynthesis |
| 9. fil1 | No | translation factor |
| 10. fpr2 | Yes | peptidyl-prolyl cis-trans isomerase |
| 11. gda1 | Yes | guanosine diphosphatase |
| 12. glo2 | Yes | Hydroxyacylglutathione hydrolase |
| 13. gre2 | Yes | alpha-acetoxy ketone reductase |
| 14. gsh2 | Yes | glutathione synthase |
| 15. hlj1 | Yes | Hsp40 chaperone in ER |
| 16. hlr1 | No | unknown, similar to Lre1 (Pke1p-MAPK pathway) |
| 17. hms1 | Yes | transcription factor |

TABLE 1-continued

Yeast strains synthetically sick or lethal with huntingtin polypeptide expression.

| Yeast Gene Deletion | Human Ortholog | Function or Proposed Function |
|---|---|---|
| 18. ipk1 | No | phosphatidylinositol phosphate kinase |
| 19. kgd1 | Yes | alpha-ketoglutarate dehydrogenase |
| 20. msb1 | Yes | activates Pke1p-MAPK pathway |
| 21. mrpl1 | No | protein of the mitochondrial large ribosomal submit |
| 22. mup1 | Yes | methionine permease |
| 23. pcl6 | No | cyclin-dependent protein kinase |
| 24. phm8 | No | possibly involved in phosphate metabolism |
| 25. prm5 | No | possible involved in cell stress |
| 26. psp1 | No | possibly involved in DNA replication |
| 27. rim4 | No | RNA binding |
| 28. sam2 | No | S-adenosylmethionine synthetase 2 |
| 29. sas3 | No | histone acetyltransferase |
| 30. sdt1 | No | 5'-Nucleotidase |
| 31. sip18 | No | binds phospholipids |
| 32. sng1 | No | probable transport protein |
| 33. stp2 | Yes | transcription factor |
| 34. Tea1 | No | transcriptional activator |
| 35. tvp15 | No | possibly involved in vesicular transport |
| 36. ubp13 | Yes | ubiquitin C-terminal hydrolase |
| 37. vps70 | Yes | possibly involved in vacuolar trafficking |
| 38. yhb1 | Yes | nitric oxide dioxygenase, oxygen transporter |
| 39. yrb30 | No | Unknown |
| 40. ybr100w | No | possibly involved in DNA damage repair |
| 41. ybr258w | No | Unknown |
| 42. ydr215c | No | Unknown |
| 43. ygr015c | No | alpha or beta hydrolase fold family |
| 44. jlr107w | No | has similarity to acyglyecrol lipase |
| 45. ykr017c | Yes | has a TRIAD composite zinc finger domain |
| 46. ykr064 | No | transcription factor |
| 47. ylrl28w | Yes | basic helix-loop-helix leucine zipper protein |
| 48. ymr160w | No | Unknown |
| 49. ynl296w | No | possibly involved in vacuolar trafficking |
| 50. yor292c | Yes | peroxisomal protein |
| 51. yor300w | No | bipolar budding and bud site selection |
| 52. ypl067c | No | Unknown |

(In column 2 of the Tables 1 and 2, "No" indicates that a human homolog has not been identified as yet, although one or more human homologs may exist and can be used in accordance with the present invention.)

TABLE 2

Yeast strains synthetically sick or lethal with α-synuclein expression.

| Yeast Gene Deletion | Human Ortholog | Function or Proposed Function |
|---|---|---|
| 1. ape2 | Yes | Aminopeptidase |
| 2. arl3 | Yes | ARF small monomeric GTPase activity |
| 3. arol | No | arom penta-functional enzyme |
| 4. cog6 | Yes | involved in vesicular transport to the Golgi |
| 5. crh1 | Yes | cell wall protein |
| 6. cvt17 | No | Lipase |
| 7. dpp1 | Yes | diacylglycerol pyrophosphate phosphatase |
| 8. fun26 | Yes | nucleoside transporter |
| 9. gip2 | Yes | regulatory subunit for PP1 phosphatase |
| 10. glo4 | Yes | hydroxyacylgluthathione hydrolase |
| 11. gtt1 | No | glutathione transferase |
| 12. hbs1 | Yes | related to translation elongation factor EF-1alpha |
| 13. hsp30 | No | heat shock protein for pH homeostatis |
| 14. ino4 | No | transcription factor (phospholipids syn genes) |
| 15. mad1 | No | involved in spindle-assembly checkpoint |
| 16. mal31 | Yes | maltose transporter |
| 17. mei4 | No | required for meiotic recombination |
| 18. met17 | Yes | O-acetylhomoserine(thiol)-lyase |

TABLE 2-continued

Yeast strains synthetically sick or lethal with α-synuclein expression.

| Yeast Gene Deletion | Human Ortholog | Function or Proposed Function |
|---|---|---|
| 19. met32 | Yes | transcription factor |
| 20. msb3 | Yes | RAB GTPase activator |
| 21. nbp2 | Yes | possibly involved in cytoskeletal organization |
| 22. nit2 | Yes | Nitrilase |
| 23. nup53 | Yes | component of nuclear pore complex |
| 24. opi3 | Yes | phosphatidylethanolamine N-methyltransferase |
| 25. pca1 | Yes | P-type copper-transporting ATPase |
| 26. pex2 | Yes | peroxisomal biogenesis protein |
| 27. pex8 | No | peroxisomal biogenesis protein |
| 28. pho13 | Yes | 4-nitrophenylphyosphatase |
| 29. pox1 | Yes | acyl-CoA oxidase |
| 30. ptk2 | Yes | serine/threonine protein kinase |
| 31. rpl41a | No | structural constituent of ribosome |
| 32. rny1 | Yes | Endoribonuclease |
| 33. sac2 | Yes | Involved in protein sorting in the late Golgi |
| 34. sap4 | No | serine/threonine phosphatase |
| 35. sod2 | Yes | manganese superoxide dismutase |
| 36. stf1 | No | ATPase inhibitor |
| 37. sip2 | Yes | transcription factor |
| 38. suv3 | Yes | mitochondrial RNA helicase (DEAD box) |
| 39. swr1 | Yes | member of Snf2p DNA helicase family |
| 40. thi7 | No | thiamine transporter |
| 41. tlg2 | Yes | syntaxin homolog (t-SNARE) |
| 42. thr1 | No | homoserine kinase |
| 43. tna1 | Yes | nicotinamide mononucleotide permease |
| 44. tsl1 | No | alpha,alpha-trehalose-phosphate synthase |
| 45. ubc8 | Yes | ubiquitin-conjugating enzyme |
| 46. vps24 | Yes | sorts proteins in the pre-vascoular endosome |
| 47. vps28 | Yes | required for traffic to vacuole |
| 48. vps60 | No | vacuolar protein sorting |
| 49. war1 | No | transcription factor |
| 50. yat1 | Yes | outer carnitine acetyltransferase, mitochondrial |
| 51. ybr013c | No | unknown |
| 52. ybr284w | No | AMP deaminase |
| 53. ybr300c | No | unknown |
| 54. yc1042w | No | unknown |
| 55. ycr026c | Yes | contains type I phosphodiesterase domain |
| 56. ycr050c | No | unknown |
| 57. ycr051wΔ | Yes | contains ankyrin (Ank) repeats |
| 58. ycr085w | No | unknown |
| 59. ydl118w | No | possibly involved in meiotic nuclear divisions |
| 60. ydr154c | No | unknown |
| 61. ydr220c | No | unknown |
| 62. yfr035c | No | unknown |
| 63. ygl109w | No | unknown |
| 64. ygl165c | No | unknown |
| 65. ygl226w | No | unknown |
| 66. ygl231c | Yes | unknown |
| 67. ygl262w | No | unknown |
| 68. ygr130c | Yes | unknown |
| 69. ygr154c | No | unknown |
| 70. ygr201c | Yes | translation elongation factor |
| 71. ygr290w | No | unknown |
| 72. yhr199c | No | unknown |
| 73. yjl118w | No | unknown |
| 74. yjl122w | No | unknown |
| 75. yjl135w | No | unknown |
| 76. yjrl54w | No | unknown |
| 77. ykl098w | No | unknown |
| 78. ykl100c | No | unknown |
| 79. ykr023w | No | unknown |
| 80. ykr035c | No | unknown |
| 81. yrl365w | No | unknown |
| 82. ylr376c | No | possibly involved in DNA repair |
| 83. ymr226c | Yes | oxidoreductase |
| 84. yml089c | No | unknown |
| 85. ymr289w | No | unknown |
| 86. yp136w | No | unknown |

Prior studies (Fernandez-Funez et al. *Nature* 408:101-06 (2000); Kazemi-Esfaijani et al., *Science* 287:1837-40 (2000)) had inherent biases and genes contributing to the toxic phenotype may have been missed. The present screens using the YGDS provided the advantage that a large percentage of genes in the yeast genome (approximately 83%) have been tested for their ability to modulate huntingtin and α-synuclein toxicity in an unbiased manner.

A low percentage of strains ins the YGDS used in this study (approximately 5-10%) may contain mutations in addition to the desired gene disruption (e.g., second-site mutations or aneuploidy) (Grunenfelder et al., *Nat. Rev. Genet.* 3:653-61 (2002)). To control for false positives due to extraneous mutations that could enhance huntingtin or α-synuclein toxicity or sensitivity, haploid deletion strains of the opposite mating type and homozygous diploid deletion strains (that lacked the same genes identified in the original screens) were transformed with plasmids expressing the huntingtin fragment or α-synuclein. A synthetic sick or lethal interaction of huntingtin and α-synuclein was reproduced in a high percentage (>95%) of these deletion strains, suggesting that the level of false positives isolated in the original screens was low.

Of the HD53Q-sensitive mutants, 77% (40/52) correspond to genes for which a function or genetic role has been determined experimentally or can be predicted (Saccharomyces Genome Database, SGD) (Table 1). 35% (14/40) of these genes clustered in the functionally related categories of cell stress, protein folding and the ubiquitin degradation pathway based on annotations in the Yeast Proteome Database. The remaining genes (26/40) were dispersed among numerous and diverse functional categories. Comparison of the relative percentages of genes in each functional category in the huntingtin screen with their relative percentage in the YGDS reveals that six functional categories (amino acid transport, nitrogen metabolism, protein folding, response to stress and ubiquitin-dependent protein catabolism) were enriched in the screen. Interestingly, 52% of the genes (27/52) identified are currently annotated as having human orthologs (Table 1, Table 3), a value that is significantly higher than the percentage of genes in the yeast genome with mammalian orthologs (approximately 31% based on a P≦value $1 \times 10^{10}$) (Botstein et al., *Science* 277:1259-60 (1997)).

TABLE 3

Human Orthologs of Yeast Genes Identified For Huntingtin Polypeptide

| Yeast gene | Human ortholog (and % identity) |
|---|---|
| APJ1 | DNAJA2 (33%); DNAJA1 (29%); DNAJB1 (25%) |
| APM2 | AP1M1 (24%); AP1M2 (24%); AP2M1 (22%) |
| AYR1 | HSD17B1 (27%); HSD17B2 (30%); RDH8 (27%) |
| CIT2 | CS (60%) |
| CMK1 | CKLIK (40%); CAMK1 (41%); CAMK1G (36%) |
| CPS1 | FLJ32569 (35%); ACY1 (39%) |
| FPR2 | FKBP2 (58%); FKBP14 (42%); FKBP10 (50%) |
| GDA1 | ENTPD6 (33%); ENTPD5 (33%); ENTPD3 (27%) |
| GLO2 | HAGH (39%); BRP17 (31%); MGC2605 (29%) |
| GRE2 | HSD3B1 (29%); H105E3 (25%) |
| GSH2 | GSS (36%) |
| HLJ1 | MGC26226 (53%); DNAJA3 (37%) |
| HMS1 | TFEB (25%); SREBF1 (36%); MITF (22%) |
| KGD1 | OGDH (45%); FLJ10851 (45%); KIAA1630 (37%) |
| MSB1 | NCOA1 (23%); MGC20460 (23%) |
| MUP1 | SLC7A9 (29%); SLC7A7 (27%); SLC7A6 (26%) |
| RIM4 | HSU53209 (33%); SFRS10 (37%); TIAL1 (22%) |
| SAM2 | MAT1A (69%); MAT2A (68%) |
| SAS3 | HTATIP (43%); HBOA (45%); RUNXBP2 (32%) |
| STP2 | LOC284459 (33%); LOC126295 (28%); OAZ (28%) |
| UBP13 | FLJ12552 (37%); USP12 (37%); USP10 (26%) |
| VPS70 | FOLH1 (26%); NAALAD2 (30%) |

TABLE 3-continued

Human Orthologs of Yeast Genes Identified For Huntingtin Polypeptide

| Yeast gene | Human ortholog (and % identity) |
|---|---|
| YHB1 | NGB (40%); HBG1 (27%) |
| YGR015C | WBSCR21 (26%) |
| YKR017C | ARIH1 (32%); ARIH2 (29%) |
| YLR128W | RP42 (25%); MGC2714 (26%); KIAA0276 (28%) |
| YOR292C | MPV17 (33%); PXMP2 (30%) |

To confirm that HD53Q induced synthetic sickness or lethality observed in yeast gene deletion strains could be rescued by expressing human orthologs of several yeast genes identified in the screen, YGDS strains having deletions in the yeast genes FPR2, GSH2 and HLJ1 were transformed with plasmids expressing the human orthologs of these genes (FKBP2, GSS or DNAJA2, respectively). Expression of the respective human ortholog rescued HD53Q induced synthetic sickness or lethality, while the empty vector alone had no effect.

Of the α-synuclein sensitive mutants that were identified in the yeast screen, 65% (56/86) correspond to genes for which a function or genetic role has been determined experimentally or can be predicted (Table 2). 32% (18/56) of these genes clustered in the functionally related categories of vesicular transport and lipid metabolism. As with the huntingtin screen, the remaining genes (38/56) were distributed among numerous functional categories. Comparison of the relative percentages of genes in each functional category in the α-synuclein screen with their relative percentage in the YGDS shows that six functional categories (lipid metabolism, peroxisome organization and biogenesis, phospholipid metabolism, protein localization, protein vacuolar targeting, and vesicle-mediated transport) are enriched in this screen. As in the huntingtin screen, a high percentage of the genes in the α-synuclein screen (50% or 43/86) are currently annotated as having human orthologs (Table 2, Table 4).

TABLE 4

Human Orthologs of Yeast Genes Identified For α-Synuclein Polypeptide

| Yeast gene | Human ortholog (and % identity) |
|---|---|
| APE2 | NPEPPS (36%); ENPEP (34%); LRAP (31%) |
| ARL3 | ARFRP1 (48%); FLJ22595 (39%); ARL5 (36%) |
| COG6 | COG6 (21%) |
| CRH1 | MUC16 (24%); KIAA2026 (31%); MUC12 (30%) |
| DPP1 | HTPAP (38%); PPAP2A (27%); PPAP2B (28%) |
| FUN26 | ENT3 (24%); SLC29A1 (23%); SLC29A2 (23%) |
| GIP2 | PPP1R3C (37%); PPP1R3B (31%); PPP1R3A (37%) |
| GLO4 | HAGH (33%); MR-1 (29%); MGC2605 (28%) |
| HBS1 | HBS1L (34%); GSPT2 (32%); GSPT1 (32%) |
| MAL31 | SLC2A2 (23%); SLC2A14 (23%); SLC2A3 (23%) |
| MET17 | CTH (32%) |
| MET32 | FLJ23436 (51%); ZNF214 (48%); ZNF132 (47%) |
| MSB3 | TBC1D8 (31%); KIAA1055 (29%); EPI64 (27%) |
| NBP2 | SH3RF (38%); SSH3BP1 (32%); SH3GL1 (38%) |
| NIT2 | NIT1 (38%); NIT2 (32%); UPB1 (25%) |
| NUP53 | LOC129401 (22%) |
| OPI3 | PEMT (44%) |
| PCA1 | ATP7B (28%); ATP7A (25%); ATP12A (25%) |
| PEX2 | PXMP3 (23%) |
| PHO13 | DJ37E16.5 (31%) |
| POX1 | ACOX1 (29%); ACOX2 (30%); ACOX3 (30%) |
| PTK2 | SSTK (31%); MARK2 (23%); STK22B (24%) |
| RNY1 | RNASE6PL (31%) |
| SAC2 | VPS52 (21%) |
| SOD2 | SOD2 (46%) |
| STP2 | LOC284459 (33%); MGC43537 (30%) |
| SUV3 | SUPV3L1 (35%); KIAA0052 (29%); DDX27 (24%) |
| SWR1 | SRCAP (48%); KIAA1259 (37%); EP400 (26%) |

TABLE 4-continued

Human Orthologs of Yeast Genes Identified For α-Synuclein Polypeptide

| Yeast gene | Human ortholog (and % identity) |
|---|---|
| TLG2 | STX16 (26%); STX1B2 (22%); STX1A (22%) |
| TNA1 | SLC17A5 (22%); C20ORF59 (23%) |
| UBC8 | UBE2H (54%); UBE2D3 (38%); UBE2A (39%) |
| VPS24 | NEDF (31%); BC-2 (25%); DKFZP564O123 (24%) |
| YAT1 | CPT2 (30%); CRAT (29%); CHAT (27%) |
| YBR284W | AMPD2 (31%); AMPD1 (28%); AMPD3 (29%) |
| YCR026C | ENPP5 (29%); ENPP3 (27%); ENPP1 (28%) |
| YCR051W | TNKS2 (35%); TNKS (35%); MIB (30%) |
| YGL231C | LOC51234 (33%) |
| YGR130C | TGOLN2 (24%); RNF111 (29%); NEDL2 (25%) |
| YGR201C | EEF1G (27%); VARS2 (29%) |
| YKL100C | HM13 (32%); SPPL2B (30%); SPPL2A (31%) |
| YKR023W | TRIP4 (25%) |
| YMR226C | RDH8 (31%); MGC4172 (34%); RETSDR2 (35%) |

The evidence indicates that genes involved in protein folding and cell stress play important roles in HD and the polyQ disorders. The appearance in diseased brains of inclusion bodies that co-localize with heat shock proteins (Hsps) and components of the ubiquitin-proteasome degradation system implies an underlying incapacity in the cellular machinery of molecular chaperones that normally functions to prevent the accumulation of misfolded proteins.

Recently, the chaperones Hsp40 and Hsp70 were suggested to prevent neurodegeneration (Fernandez-Funez et al. *Nature* 408:101-06 (2000); Kazemi-Esfarani et al., *Science* 287:1837-40 (2000); Cummings et al., *Hum. Mol. Genet.* 10:1511-81 (2001); Warrick et al., *Nat. Genet.* 23:425-28 (1999)). Additional support for an important role of genes in cell stress and protein folding pathways comes from genetic screens in *Drosophila* to identify modifiers of polyQ-induced toxicity. Two genes suppressed polyQ toxicity, one encoding a *Drosophila* homolog of human Hsp40/HDJ1 (dHDJ1), a co-chaperone for Hsp70 in vivo, and the other encoding a *Drosophila* homolog of human tetratricopeptide repeat protein 2 (Kazemi-Esfarjani et al., *Science* 287:1837-40 (2000)). In an independent study, dMJ1 was isolated as a suppressor of polyQ-mediated toxicity induced by the expression of full length human SCA1 in fruitflies (Fernandez-Funez et al., *Nature* 408:101-06 (2000)).

While these studies show that over expression of Hsp40 genes suppresses neurodegeneration, the yeast screen identifies two Hsp40 homologs (Apj1 and Hlj1) that when deleted unmask or potentiate toxicity of a mutant huntingtin fragment. These results indicate that in wild-type yeast cells, Hsp40 chaperones are necessary to suppress polyQ toxicity. In addition to chaperones, 8 genes (FPR2, GPE2, GSH2, HLR1, PRM5, SIP18, YHB1, YJR107W) involved in various forms of cellular stress (osmotic, oxidative, nitrosative) were identified in the screen as enhancers of huntingtin toxicity.

In contrast to the results from the huntingtin screen, genes in stress response pathways were not enriched significantly in the α-synuclein screen, despite the fact that both huntingtin and α-synuclein form aggregates and inclusion bodies with similar physical, biochemical and morphological properties in yeast. α-Synuclein is an abundant brain protein that is in a family with at least three members (α, β and γ-synuclein); however, the functions of these proteins are poorly understood (Goedert, *Nat. Rev. Neurosci.* 2:492-501 (2001)). α- and β-synuclein localize to nerve terminals and may be associated with synaptic vesicles, based on immunohistochemistry and ultrastructural analyses (Clayton et al., *J. Neurosci. Res.* 58:120-29 (1999)). α-synuclein interacts with synphilin-1 (Engelentler et al., *Nat. Genet.* 22:110-14 (1999)), which has been proposed to function as an adaptor protein linking α-synuclein to proteins involved in vesicular transport. Although the function of α-synuclein is still not clear, this protein has been linked to learning, development and plasticity (George et al., *Neuron* 15:361-72 (1995)), and most likely plays a role in synaptic vesicle recycling. Interestingly, recent in vitro studios suggest that pre-fibrillar intermediates called protofibrils formed by α-synuclein can bind and permeabilize acidic phospholipid vesicles (Volles et al., *Biochemistry* 40:7812-19 (2001)), which has been proposed to lead, to defective sequestration of dopamine into vesicles and subsequent generation of reactive oxygen species in the cytoplasm that contribute to neuronal dysfunction and cell death (Lotharius et al., *Nat. Rev. Neurosci.* 3:932-42 (2002)). The yeast screen for modifiers of α-synuclein toxicity identified 32% (18/56) of genes of known function that are involved in vesicular tracking or lipid metabolism pathways. As 72% (13/18) of these genes have human orthologs, these results help elucidate the normal cellular function of α-synuclein and identify downstream interacting proteins that may play roles in PD pathogenesis.

The results of this study indicate that toxicity mediated by α-synuclein and a mutant huntingtin fragment is regulated by non-overlapping sets of conserved genes and pathways. The major functional categories enriched in the α-synuclein genetic screen did not overlap with any of the major categories observed in the huntingtin screen, and only 1/138 genetic modifiers were found in common to both screens. These results are consistent with studies in yeast showing that α-synuclein, and not a mutant huntingtin fragment, localizes to membranes, inhibits phospholipase D and vesicular trafficking. Taken together, these results suggest that at least in yeast, toxicity is likely to be upstream of the process of inclusion, body formation. Consistent with this interpretation, no correlation between levels of aggregation and extent of toxicity was detected in deletion strains sensitive to huntingtin. As neurodegeneration in HD and PD involve a complex, multigenic mechanisms, it is important to determine the genes and cellular pathways that are of primary significance for neuronal dysfunction and cell death. The yeast synthetic screens, combined with other molecular genetic approaches in this and other model organisms, help elucidate these complex cellular pathways. These results also help guide ongoing human genetic studies aimed at discovering genetic modifiers for age of onset is HD, and new disease loci that segregate with inherited forms of PD.

Example 2

Using the methods described supra (see Example 1), the yeast gene deletion strains aro9Δ and npt1Δ were also identified as enhancers of polyQ toxicity (sick or lethal with huntingtin polypeptide expression). The gene product of aro9 (ARO9—aromatic amino acid aminotransferase II) has been identified as having kynurenine-oxoglutarate transaminase and aromatic-amino-acid transaminase activities. Human orthologs of ARO9 include AADAT (26% identity) and CCBL1 (23% identity). The gene product of npt1 (NPT1) is a nicotinate phosphoribosyltransferase (NAPRTase) that catalyzes the first step in the Preiss-Handler pathway.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying an agent for diminishing cellular toxicity associated with an α synuclein polypeptide of Parkinson's disease, comprising:
   contacting a yeast cell with a candidate agent, wherein the yeast cell expresses an α synuclein polypeptide and the cell does not express an endogenous wild-type gene, wherein the absence of the endogenous wild-type gene expression causes or enhances toxicity associated with the presence of the α synuclein polypeptide, and wherein the endogenous wild-type gene is selected from vps24 and vps28; and
   determining whether the candidate agent reduces toxicity of the α synuclein polypeptide, wherein the method comprises comparing the viability of the cell contacted with the candidate agent with the viability of a control cell not contacted with the candidate agent.

2. The method of claim 1, further comprising re-screening at least one identified candidate agent to confirm that the identified agent reduces toxicity associated with the α synuclein polypeptide.

3. The method of claim 2, wherein the re-screening comprises
   contacting a second yeast cell with the candidate agent, wherein the second yeast cell expresses the α synuclein polypeptide and does not express the endogenous wild-type gene which causes or enhances toxicity in the presence of the α synuclein polypeptide, and wherein expression of the α synuclein polypeptide is toxic to the second yeast cell; and
   determining whether the candidate agent reduces toxicity associated with the α synuclein polypeptide on the second yeast cell.

4. The method of claim 1, wherein the α synuclein polypeptide is wild-type α synuclein.

5. The method of claim 1, wherein the α synuclein polypeptide is a mutant.

6. The method of claim 1, wherein the yeast cell is a *Saccharomyces cerevisiae* cell.

7. The method of claim 1, wherein the yeast cell does not express endogenous wild-type vps24 and vps28.

8. The method of claim 1, wherein the candidate agent is a small molecule, a nucleic acid, a proteinaceous agent, or a peptidomimetic.

9. The method of claim 1, wherein the candidate agent is a synthetic compound.

10. The method of claim 1, wherein the candidate agent is a natural compound.

* * * * *